(12) United States Patent
Newell et al.

(10) Patent No.: US 7,445,794 B1
(45) Date of Patent: *Nov. 4, 2008

(54) METHODS FOR TREATING HUMAN PROLIFERATIVE DISEASES, WITH A COMBINATION OF FATTY ACID METABOLISM INHIBITORS AND GLYCOLYTIC INHIBITORS

(75) Inventors: Martha Karen Newell, Colorado Springs, CO (US); Elizabeth Villobos-Menuey, Monument, CO (US); Evan Newell, Menlo Park, CA (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/119,000

(22) Filed: Apr. 28, 2005

Related U.S. Application Data

(60) Provisional application No. 60/566,746, filed on Apr. 29, 2004.

(51) Int. Cl.
*A61K 39/395* (2006.01)
*A61K 31/675* (2006.01)
*A01N 43/04* (2006.01)

(52) U.S. Cl. .................. 424/450; 424/146.1; 424/130.1; 424/138.1; 424/141.1; 514/27; 514/43; 514/79

(58) Field of Classification Search .......... None
See application file for complete search history.

(56) References Cited

U.S. PATENT DOCUMENTS 6,670,330 B1  12/2003  Lampidis
2005/0020682 A1*  1/2005  Newell et al. ............... 514/560

2006/0140953 A1*  6/2006  Newell et al. ............ 424/146.1

FOREIGN PATENT DOCUMENTS

EP  239 400 A2  9/1987

OTHER PUBLICATIONS

Clement et al., EMBO J. Jan. 15, 1996; 15(2):216-225.*
Li et al., Endocrinology. Apr. 2002; 143(4):1371-1377.*
Kuhajda et al., PNAS USA. Mar. 28, 2000; 97(7): 3450-3454; Epub Mar. 14, 2000.*
Black et al., Cancer Res. May 1, 1949; 9:314-319, Abstract Only.*
Alberts et al., Molecular Biology of the Cell. Fourth Ed. Garland Science. 2002. New York, at p. 856-857 and Figure 15-32.*
Calkins et al., UNL Beef Cattle Reports. University of Nebraska Cooperative Extension—MP71, BEEF. Feb. 1999.*
Strieleman et al., J Biol Chem. Nov. 5, 1985; 260(25):13402-13405.*
Cabrero et al., Biochemica et Biophysica Acta. 2001; 1532:195-202, abstract.*

* cited by examiner

*Primary Examiner*—Manjunath Rao
*Assistant Examiner*—Cherie M. Woodward
(74) *Attorney, Agent, or Firm*—Wolf, Greenfield & Sacks, P.C.

(57) ABSTRACT

The present invention generally relates to systems and methods for treating inflammatory and proliferative diseases, and wounds, using a combination of (1) fatty acid metabolism inhibitors and (2) glycolytic inhibitors and/or UCP and/or Fas inhibitors or antibodies. More particularly, the invention combines an oxirane carboxylic acid compound, represented by etomoxir, with a 2-deoxyglucose compound, represented by 2-deoxy-D-glucose, and/or an antibody against UCP and/or Fas antigen. The systems and methods of the invention can be used to treat drug-resistant or multi-drug resistant cancers (i.e., cancers resistant to conventional cancer drug therapies).

10 Claims, 13 Drawing Sheets

No Treatment = 31% Death
Eto Treatment = 57% Death
2D Treatment = 46% Death
Both Treatments = 66% Death
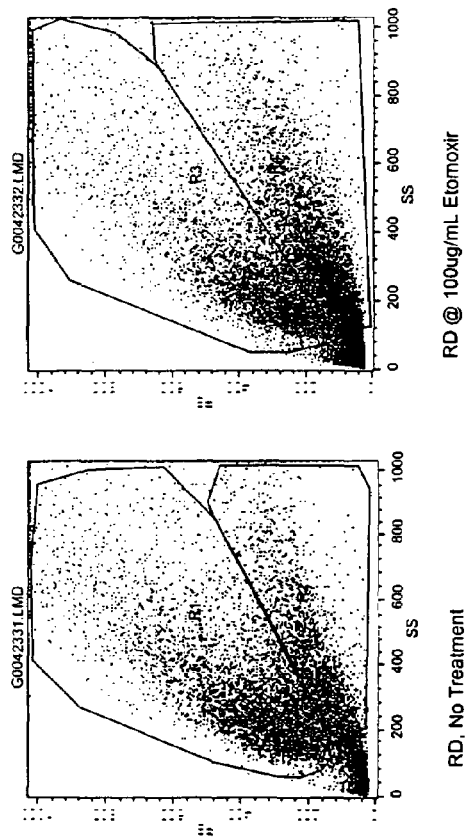
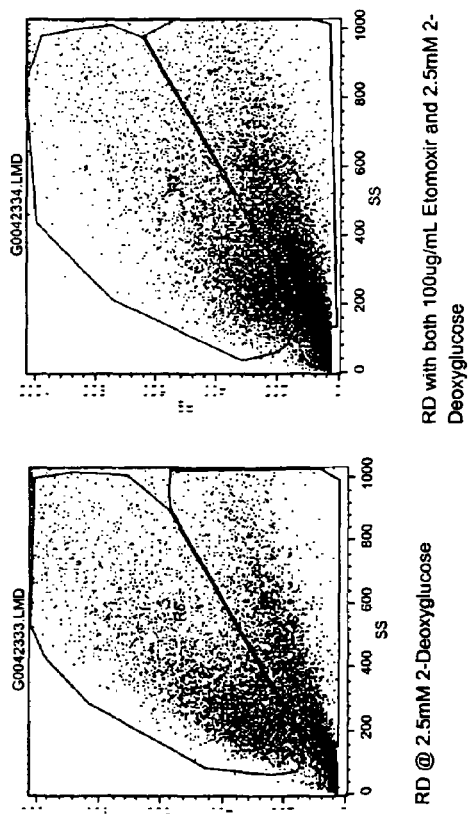
FIG. 3
RD Cells Treated or not with Etomoxir or 2-Deoxyglucose
24 Hours

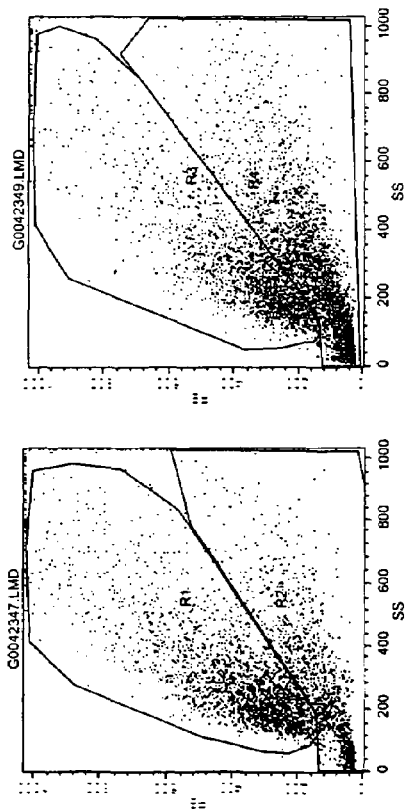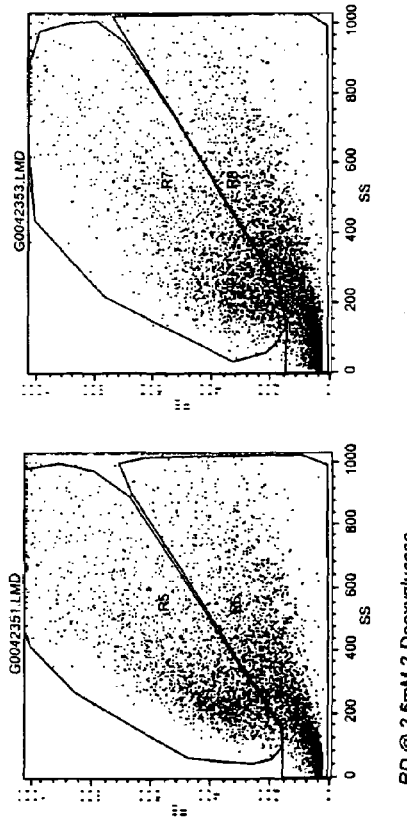
FIG. 7
No Treatment = 36% Death
Eto Treatment = 64% Death
2D Treatment = 63% Death
Both Treatments = 68% Death
RD Cells Treated or not with Etomoxir, 2-Deoxyglucose, or Both
48 Hours No Treatment = 16% Death
Eto Treatment = 9% Death
2D Treatment = 36% Death
Both Treatments = 100% Death
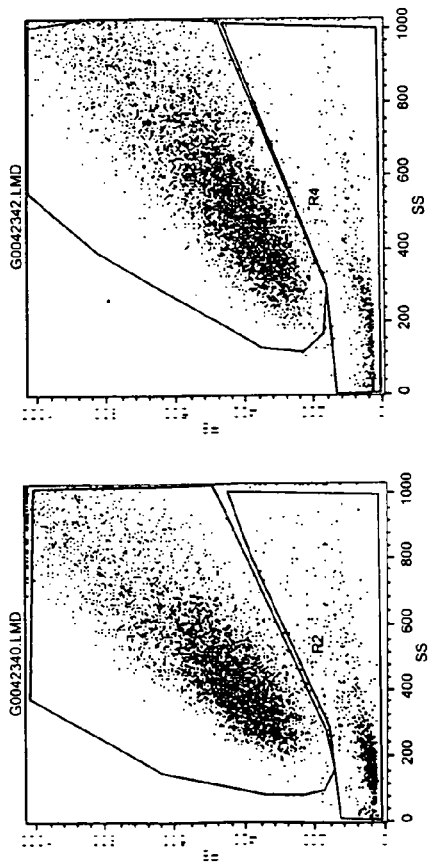
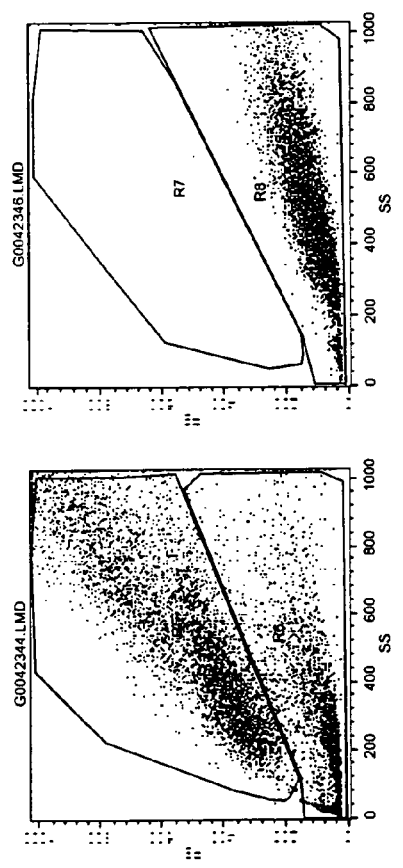
FIG. 9
HL60 MDR Cells Treated or not with Etomoxir, 2-Deoxyglucose, or Both AND with anti-UCP2 antibody
48 Hours

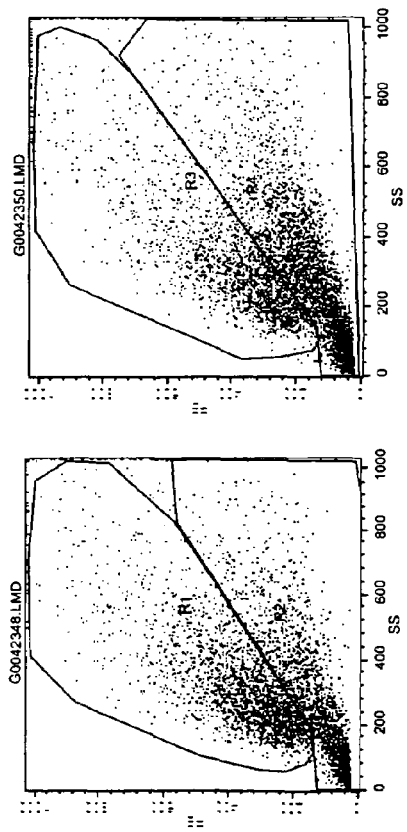
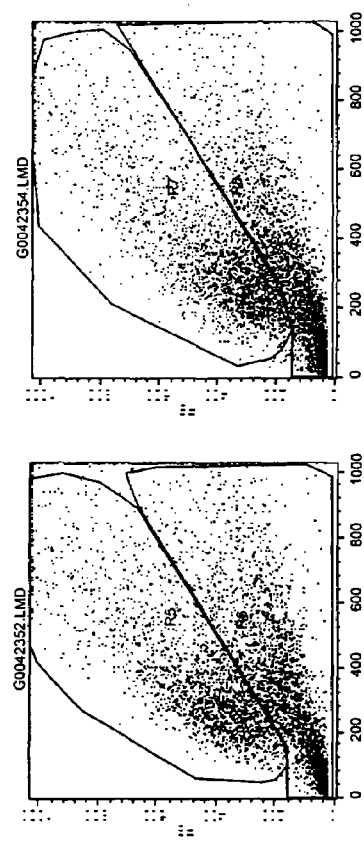
FIG. 11

METHODS FOR TREATING HUMAN PROLIFERATIVE DISEASES, WITH A COMBINATION OF FATTY ACID METABOLISM INHIBITORS AND GLYCOLYTIC INHIBITORS

RELATED APPLICATIONS

This application claims the benefit of: U.S. Provisional Patent Application Ser. No. 60/566,746, filed Apr. 29, 2004, entitled "Systems and Methods for Treating Human Inflammatory and Proliferative Diseases, With a Combination of Fatty Acid Metabolism Inhibitors and Glycolytic Inhibitors and/or UCP and/or Fas antibodies," by Karen Newell.

FIELD OF INVENTION

This invention generally relates to systems and methods for treating human inflammatory and proliferative diseases, and wounds.

BACKGROUND

Normal tissue develops, and is maintained by, processes of cell division and cell death. In many diseases, such as cancer, diabetes mellitus Type I, and autoimmune disease, the normal balance between cell division and cell death is disrupted, causing either a rapid growth of unwanted and potentially dangerous cells, and/or a loss of cells essential to maintaining the functions of tissue.

Inappropriate cell division or cell death can result in serious life-threatening diseases. Diseases associated with increased cell division include cancer and atherosclerosis. Disease resulting from increased cell death includes AIDS, neurodegenerative diseases (e.g., Alzheimer's disease, Parkinson's disease, amyotrophic lateral sclerosis, retinitis pigmentosa), aplastic anemia, atherosclerosis (e.g., myocardial infarction, stroke, reperfusion injury), and toxin induced liver disease.

It has recently been discovered that uncoupling protein ("UCP") is present in the membranes of cells other than in the mitochondria. For instance, it has been discovered that UCP is present in the plasma membrane of rapidly dividing cells. It was found that the UCP in the plasma membrane plays an important role in the signal processes which determine whether a cell will undergo cellular division, cellular differentiation, or cellular death. This finding has important implications for treating diseases associated with excessive cellular division, aberrant differentiation, and premature cellular death, e.g., for the treatment of cancers, autoimmune disease, degenerative diseases, regeneration, etc.

Several cell surface proteins have previously been identified as cell death proteins. These proteins are believed to be involved in initiating a signal, which instructs the cell to die. Cell death proteins include, for example, Fas/CD95 (Trauth, et al., *Science,* 245:301, 1989), tumor necrosis factor receptors, immune cell receptors such as CD40, OX40, CD27 and 4-1BB (Smith, et al., *Cell,* 76:959, 1994), and RIP (U.S. Pat. No. 5,674,734). These proteins are believed to be important mediators of cell death. These mediators, however, do not always instruct a cell to die. In some cases, these mediators actually instruct a cell to undergo cell division. The intracellular environment, and particularly the status of the proton motor force and the source of fuel for mitochondrial metabolism, determines whether stimulation of the cell death protein will lead to a signal for death or cell division (see, e.g., co-pending U.S. patent application Ser. No. 09/277,575, incorporated herein by reference).

UCP can regulate cell division by manipulating the manner in which the cell processes and utilizes energy. It has been discovered that UCP is normally present on the plasma membrane of rapidly dividing cells, but is not typically found on the plasma membrane of growth-arrested or chemotherapy-resistant tumor cells. These findings have important implications on the ability to regulate cell division as well as sensitivity and resistance to chemotherapeutic agents.

It is commonly observed in treating cancers, that initial treatments, such as with chemotherapy and/or radiation therapy, are effective to destroy significant numbers of tumor cells, only to leave behind a small number of tumor cells that are resistant to the treatment, which then multiply to form newly detected tumors that are increasingly resistant to treatment as new rounds of therapy are tried. The growing popularity of "cocktails" of chemotherapy drugs has given rise to multidrug resistant ("MDR") tumor cells, which are ever more difficult to destroy. Drug sensitive tumor cells, under the selective pressure of treatment with drugs, develop into drug resistant versions of the same tumor cell type. Drug resistance, either acquired or inherent, is the leading cause of death in cancer. Methods for dealing with MDR tumor cells have been proposed, but without practical, clear clinical success at entirely eliminating such cells and providing a cure for patients with MDR tumors. For example, in Lampdis and Priebe U.S. Pat. No. 6,670,330, entitled: "Cancer Chemotherapy with 2-Deoxy-D-Glucose", incorporated herein in its entirety by reference, a class of glycolytic inhibitors are described for use in combination with standard chemotherapy protocols in treating solid tumors by attacking anaerobic cells a the center of the tumor. In Pizer, Townsend and Kuhajda U.S. Patent Publication No. 20020187534, published Dec. 12, 2002, entitled: "Treating cancer by increasing intracellular malonyl CoA levels," incorporated herein in its entirety by reference, fatty acid metabolism is manipulated by inhibition of carnitine palmitoyltransferase-1, for example with etomoxir.

SUMMARY OF INVENTION

The invention generally relates to systems and methods for treating inflammatory and proliferative diseases, and wounds, using a combination of (1) fatty acid metabolism inhibitors and (2) glycolytic inhibitors and/or UCP and/or Fas inhibitors or antibodies. More particularly, the invention combines an oxirane carboxylic acid compound, represented by etomoxir, with a 2-deoxyglucose compound, represented by 2-deoxy-D-glucose, and/or an antibody against UCP and/or Fas antigen.

In one aspect, the invention comprises a method. In one set of embodiments, the method includes exposing a cell to a combination of glycolytic inhibitor and a fatty acid metabolism inhibitor, i.e., an inhibitor of fat burning. In another set of embodiments, the method includes increasing the amount of UCP and/or Fas on the surface of a cell, e.g., by means of a fatty acid metabolism inhibitor, and exposing the cell to a UCP and/or Fas antibody, e.g., exposing a cell to a fatty acid metabolism inhibitor and, preferably thereafter, to an antibody to UCP or to a Fas antigen.

The invention, in another aspect, includes a composition. In one set of embodiments, the composition includes a cell exposed to both a glycolytic inhibitor and a fatty acid metabolism inhibitor. The invention, in another set of embodiments, includes the glycolytic inhibitor and fatty acid metabolism inhibitor in combination with a pharmaceutically acceptable carrier. In still another set of embodiments, the composition includes a fatty acid metabolism inhibitor in combination with an antibody to UCP or to a Fas antigen.

In yet another aspect, the invention is a kit. In one set of embodiments, the kit includes at least the glycolytic inhibitor and the fatty acid metabolism inhibitor. In another set of embodiments, the kit includes a fatty acid metabolism inhibitor and an antibody to UCP or to a Fas antigen.

In another aspect, the present invention is directed to a method of making one or more of the embodiments described herein. In yet another aspect, the present invention is directed to a method of using one or more of the embodiments described herein. In still another aspect, the present invention is directed to a method of promoting one or more of the embodiments described herein.

Other advantages and novel features of the invention will become apparent from the following detailed description of the various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

FIG. 3 is a dot plot as a function of live versus dead RD cells untreated or treated with etomoxir, 2-deoxy-D-glucose, or both, at the indicated concentrations for 24 hours;

FIG. 7 is a dot plot as a function of live versus dead RD cells untreated or treated with etomoxir, 2-deoxy-D-glucose, or both, at the indicated concentrations for 48 hours;

FIG. 9 is a dot plot as a function of live versus dead HL60 MDR cells, treated with anti-UCP2 antibody and otherwise untreated or treated with etomoxir, 2-deoxy-D-glucose, or both, at the indicated concentrations for 48 hours;

FIG. 11 is a dot plot as a function of live versus dead RD cells, treated with anti-UCP2 antibody and otherwise untreated or treated with etomoxir, 2-deoxy-D-glucose, or both, at the indicated concentrations for 48 hours;

BRIEF DESCRIPTION OF THE SEQUENCE

Figure 1:
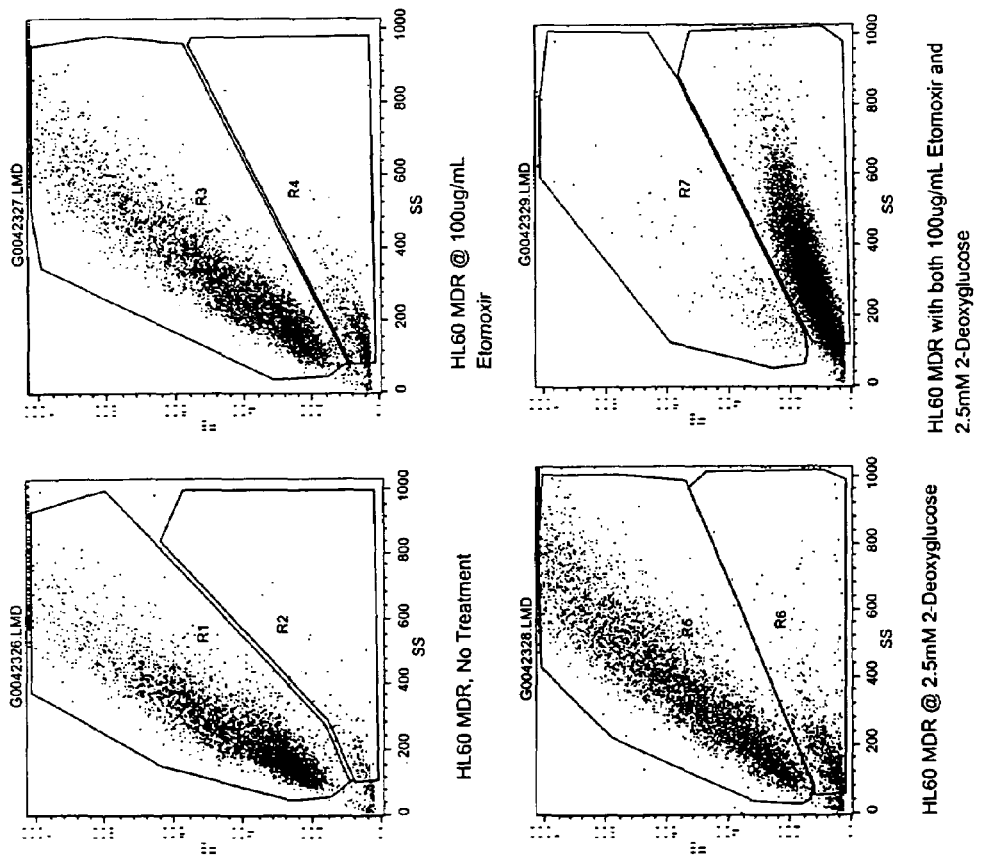
FIG. 1 is a dot plot as a function of live versus dead multidrug resistant human leukemia cell HL60 MDR untreated or treated with etomoxir, 2-deoxy-D-glucose, or both, at the indicated concentrations for 24 hours.

SEQ ID NO:1 is the nucleotide sequence of the human uncoupling (UCP-1) cDNA with GenBank Acc. No. U28480;

SEQ ID NO:2 is the predicted amino acid sequence of the translation product of human uncoupling cDNA (UCP-1) (SEQ ID NO:1);

SEQ ID NO:3 is the nucleotide sequence of the human uncoupling (UCP-2) cDNA with GenBank Acc. No. U82819;

SEQ ID NO:4 is the predicted amino acid sequence of the translation product of human uncoupling cDNA (UCP-2) (SEQ ID NO:3);

SEQ ID NO:5 is the nucleotide sequence of the human uncoupling (UCP-3S) cDNA with GenBank Acc. No. U82818; and SEQ ID NO:6 is the predicted amino acid sequence of the translation product of human uncoupling cDNA (UCP-3S) (SEQ ID NO:5).

DETAILED DESCRIPTION

The present invention proceeds by recognizing that cells have available to them a number of different metabolic pathways that are brought into play depending on the nature and degree of stress applied to the cells, that cell apoptosis is brought about to a significant extent because the target cells are recognized by the immune system, and that MDR cells are to a significant extent invisible to the immune system. The invention targets cellular metabolic pathways of defective cells, tissues or organs, and the immune system to treat human inflammatory and proliferative diseases, such as cancer, autoimmunity, heart disease, and chronic infectious disease. The methods herein are also useful in tissue regeneration, including neural regeneration, transplantation, and wound healing.

Every cell in the body uses carbohydrates, protein, and fat in different proportions for energy. The cell's choice of fuel, its metabolic strategy, will change depending on its state of activation or differentiation. For example, a cell that is rapidly dividing has different energy demands than one that is not dividing. The same is true for cells that are under stress or are infected. The present invention proceeds from the discovery of a unique metabolic strategy, widely used by drug resistant cells, that is characterized by the ability to burn fat under conditions of stress, including the stress of chemotherapy or radiation. When cells are rapidly dividing, they use glucose at very high rates, but under conditions of stress, cells, if capable, use fat in a greater proportion as a protective strategy. Respiration, oxygen use, and external stresses can generate a variety of toxic by-products (including free radicals) that can cause damage to cells. Tumor cells upregulate proteins that allow them to burn fat as a protective strategy against such by-products. The immune system can monitor the metabolic state of individual cells and destroy those in an inappropriate state. However, tumor cells can survive this surveillance by changing their metabolic strategy to one that protects the tumor cell by causing the cell to be invisible to the immune system.

By inhibiting fatty acid metabolism, the cell is forced to resume glucose metabolism, thus exhibiting UCP and/or Fas on its cell surface to become visible to the immune system. Thus the invention generally relates to systems and methods for treating inflammatory and proliferative diseases, and wounds, using a combination inhibitors that target both predominant metabolic pathways: (1) a fatty acid metabolism inhibitor and (2) a glycolytic inhibitor. As a result of inhibition of fatty acid metabolism, UCP and/or Fas is exposed on the cell surface so that the cell becomes susceptible to attack by an antibody. Accordingly, in another, or further, embodiment, along with, preferably after, treatment of the MDR cell with a fatty acid inhibitor, it is subjected to a UCP and/or Fas antibody.

More particularly, the fatty acid metabolism inhibitor is an oxirane carboxylic acid compound, exemplified by etomoxir, and the glycolytic inhibitor is a 2-deoxyglucose compound, exemplified by 2-deoxy-D-glucose.

Uncoupling proteins (UCPs) are often expressed in the plasma membrane of rapidly dividing cells. By manipulating UCP expression within cellular and intracellular membranes, inhibition of cellular, metabolic, and/or immunological responses may occur. In the present invention, the cells can be manipulated to increase the amount of UCP in the plasma membrane in some Fashion (and/or decrease mitochondrial UCP). The cells may also be manipulated to increase the amount of cell surface Fas, for example, by exposure to the fatty acid metabolism inhibitor as a source of energy in the mitochondria.

The following applications are incorporated herein by reference: U.S. Provisional Patent Application Ser. No. 60/566,746, filed Apr. 29, 2004, entitled "Systems and Methods for Treating Human Inflammatory and Proliferative Diseases, With a Combination of Fatty Acid Metabolism Inhibitors and Glycolytic Inhibitors and/or UCP and/or Fas antibodies"; U.S. patent application Ser. No. 11/031,109, filed Jan. 7, 2005, entitled "Systems and Methods for Treating Human Inflammatory and Proliferative Diseases, With UCP and/or Fas Antibody or Other Inhibitor, Optionally With a Fatty Acid Metabolism Inhibitors and/or Glucose Metabolism Inhibitor"; International Patent Application No. PCT/US2004/018612, filed Jun. 11, 2004, published as WO 2004/111199, entitled "Systems and Methods for Treating Human Inflammatory and Proliferative Diseases and Wounds, With Fatty Acid Metabolism Inhibitors and/or Glycolytic Inhibitors"; and International Patent Application No. PCT/US2000/17245, filed Jun. 22, 2000, published as WO 2000/78941, entitled "Methods and Products for Manipulating Uncoupling Protein Expression."

The indefinite articles "a" and "an," as used herein in the specification and in the claims, unless clearly indicated to the contrary, should be understood to mean "at least one."

As used herein, "or" is understood to mean inclusively or, i.e., the inclusion of at least one, but including more than one, of a number or list of elements. Only terms clearly indicated to the contrary, such as "exclusively or" or "exactly one of," will refer to the inclusion of exactly one element of a number or list of elements.

A "subject," as used herein, means a human or non-human mammal, including but not limited to, a dog, cat, horse, cow, pig, sheep, goat, chicken, primate, rat, and mouse.

The systems and methods of the invention have broad utility in regulating mammalian cell growth and death in vitro, in vivo, and ex vivo. The in vitro methods of the invention are useful for a variety of purposes. For instance, the systems and methods of the invention may be useful for identifying drugs, which have an effect, such as a preventative effect, on cellular division, cancers, or cell death, by contacting cells manipulated by the invention to undergo cellular division or death upon exposure to putative compounds.

In addition to in vitro methods, certain methods of the invention may be performed in vivo or ex vivo in a subject to manipulate one or more cell types within the subject. An "ex vivo" method, as used herein, is a method, which involves isolation of a cell from a subject, manipulation of the cell outside of the body, and reimplantation of the manipulated cell into the subject. The ex vivo procedure may be used on autologous or heterologous cells, and is typically used on autologous cells. In some embodiments, the ex vivo method is performed on cells that are isolated from bodily fluids, such as peripheral blood or bone marrow; however, the cells may be isolated from any source of cells. When returned to the subject, the manipulated cell can be programmed for cell death or division, depending on the treatment to which it was exposed. Ex vivo manipulation of cells has been described in several references in the art, including Engleman, *Cytotechnology*, 25:1, 1997; Van Schooten, et al., *Molecular Medicine Today*, June, 255, 1997; Steinman, *Experimental Hematology*, 24:849, 1996; and Gluckman, *Cytokines, Cellular and Molecular Therapy*, 3:187, 1997. The ex vivo activation of cells of the invention may be performed by routine ex vivo manipulation steps known in the art.

In vivo methods are also well known in the art. Thus, the invention is useful for therapeutic purposes as well as research purposes, such as testing in animal or in vitro models of certain medical, physiological or metabolic pathways or conditions.

One or more of the inhibitors may be an isolated molecule in certain cases. An "isolated molecule," as used herein, is a molecule that is substantially pure and is free of other substances with which it is ordinarily found in nature or in vivo systems to an extent practical and appropriate for its intended use. In particular, the molecular species may be sufficiently pure and may be sufficiently free from other biological constituents of host cells so as to be useful in, for example, producing pharmaceutical preparations, or for sequencing, e.g., if the molecular species is a nucleic acid, peptide, or polysaccharide. Because an isolated molecular species of the invention may be admixed with a pharmaceutically acceptable carrier in a pharmaceutical preparation, and/or other physiologically active agents, the molecular species may comprise only a small percentage by weight of the preparation. The molecular species is nonetheless substantially pure in that it has been substantially separated from the substances with which it may be associated in living systems.

Fatty Acid Metabolism Inhibitor

The fatty acid metabolism inhibitor used herein is an oxirane carboxylic acid compound able to inhibit (e.g., prevent, or at least decrease the activity by an order of magnitude or more) a reaction within the fatty acid metabolism pathway, such as an enzyme-catalyzed reaction within the pathway. The inhibitor may inhibit the enzyme, e.g., by binding to the enzyme to interfere with operation of the enzyme (for example, by blocking an active site or a docking site, altering the configuration of the enzyme, competing with an enzyme substrate for the active site of an enzyme, etc.), and/or by reacting with a coenzyme, cofactor, etc. necessary for the enzyme to react with a substrate. The fatty acid metabolism pathway is the pathway by which fatty acids are metabolized within a cell for energy (e.g., through the synthesis of ATP and the breakdown of fatty acids into simpler structures, such as $CO_2$, acyl groups, etc.).

The fatty acid metabolism pathway includes several enzymatic reactions, for example, using enzymes such as reductases or isomerases. Specific examples of enzymes within the fatty acid metabolism pathway include 2,4-dienoyl-CoA reductase, 2,4-dienoyl-CoA isomerase, butyryl dehydrogenase, etc. In one set of embodiments, the fatty acid metabolism inhibitor is an inhibitor able to inhibit a beta-oxidation reaction in the fatty acid metabolism pathway. In another set of embodiments, the inhibitor is an inhibitor for a fatty acid transporter (e.g., a transporter that transports fatty acids into the cell, or from the cytoplasm into the mitochondria for metabolism), the inhibitor may react or otherwise inhibit key steps within the fatty acid metabolism pathway, or the inhibitor may be an inhibitor of fatty acids as a source of energy in the mitochondria. For example, the inhibitor may inhibit the breakdown of intermediates such as butyryl CoA, glutaryl CoA, or isovaleryl CoA. In one embodiment, the inhibitor is a non-hydrolyzable analog of carnitine.

2,4-dienoyl-CoA reductase is an enzyme that catalyzes reduction reactions involved in the metabolism of polyunsaturated fatty acids. The fatty acid may be a substrate for the 2,4-dienoyl-CoA reductase within the mitochondria. In some cases, fatty acids may be transported into the mitochondria through uncoupling proteins. Additionally, the uncoupling protein may increase the mitochondrial metabolism to increase the throughput of beta-oxidation to increase the availability of the substrate.

2,4-dienoyl-CoA isomerase is an enzyme that catalyzes isomerization of certain fatty acids. One step in the metabolism of certain polyunsaturated fatty acids may be protective against reactive oxygen intermediates. Thus, by generating substrates and antagonists for the activity of 2,4-dienyol-CoA isomerase, the production of reactive oxygen intermediates may be enhanced and/or reduced. This, in turn, may affect certain disease states, such as cancer.

It is to be understood that, as used herein, the oxirane carboxylic acid compound fatty acid metabolism inhibitor is also useful for altering cellular production of reactive oxygen; thus, the oxirane carboxylic acid compounds described in reference to fatty acid metabolism inhibition should also be understood herein to be able to alter reactive oxygen production within a cell. For example, by altering the ability of a cell to metabolize a fatty acid, the ability of the cell to produce reactive oxygen may also be affected since one pathway for a cell to produce reactive oxygen intermediates ("ROI") is through the metabolism of fatty acids. Alteration of the production of reactive oxygen in a cell may be associated with changes in the immune profile of cells, i.e., how immune cells respond to the cell. Thus, in some cases, exposing a cell to, or removing a cell from, a fatty acid metabolism inhibitor can affect the production of reactive oxygen. The alteration of the production of reactive oxygen may be useful in treating cancer and/or enhancing wound healing, as the alteration of the immune profile of cells within the cancer site or the wound may stimulate the immune system and/or other wound-healing processes.

Preferred oxirane carboxylic acid compounds have the formula:

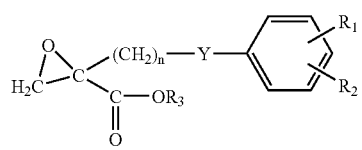

wherein: $R_1$ represents a hydrogen atom, a halogen atom, a 1-4C alkyl group, a 1-4C alkoxy group, a nitro group or a trifluoromethyl group; $R_2$ has one of the meanings of $R_1$; $R_3$ represents a hydrogen atom or a 1-4C alkyl group; Y represents the grouping —O—$(CH_2)_m$—; m is 0 or a whole number from 1 to 4; and n is a whole number from 2 to 8 wherein the sum of m and n is a whole number from 2 to 8. More preferred are oxirane carboxylic acid compounds wherein $R_1$ is a halogen atom, $R_2$ is a hydrogen atom, m is 0, and n is 6, and more particularly where $R_3$ is an ethyl group. It is most particularly preferred to use etomoxir, i.e., 2-(6-(4-chlorophenoxy)-hexyl)-oxirane-2-carboxylic acid ethyl ester.

As used herein, the term "halogen," or equivalently, "halogen atom," is given its ordinary meaning as used in the field of chemistry. The halogens include fluorine, chlorine, bromine, iodine, and astatine. Preferably, the halogen atoms used in the present invention include one or more of fluorine, chlorine, bromine, or iodine. In certain embodiments of the invention, the halogen atoms found within the structure are fluorine, chlorine, and bromine; fluorine and chlorine; chlorine and bromine, or a single type of halogen atom.

Examples oxirane carboxylic acid compounds useful in the invention are: 2-(6-(4-chlorophenoxy)-hexyl)-oxirane-2-carboxylic acid ethyl ester, 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5-(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxy-hexyl)-oxirane-2-carboxylic acid ethyl ester, the corresponding oxirane carboxylic acids, and their pharmacologically acceptable salts. It is most particularly preferred to use etomoxir, i.e., 2-(6-(4-chlorophenoxy)-hexyl)-oxirane-2-carboxylic acid ethyl ester.

Some of the compounds described herein are commercially available compounds, are derived from commercially available compounds, or are synthesized de novo using routine chemical synthetic procedures known to those of ordinary skill in the art and/or described herein.

In some embodiments, the systems and methods of the invention described herein may include homologs, analogs, derivatives, enantiomers and/or functionally equivalent compositions thereof of the fatty acid metabolism inhibitors and/or agents able to alter cellular production of reactive oxygen described herein. Such homologs, analogs, derivatives, enantiomers and functionally equivalent compositions thereof may be used in any of the systems and methods described herein. "Functionally equivalent" also refers to compositions capable of treatment of a subject that is wounded or exhibits symptoms of cancer (or other conditions described herein), a subject susceptible to or otherwise at increased risk for cancer, or a subject not exhibiting symptoms of cancer, but for whom it is desired to decrease the risk of cancer (e.g., a vaccination or a prophylactic treatment), etc. It will be understood that one of ordinary skill in the art will be able to manipulate the conditions in a manner to prepare such homologs, analogs, derivatives, enantiomers and functionally equivalent compositions as necessary. Homologs, analogs, derivatives, enantiomers and/or functionally equivalent compositions that are about as effective or more effective than the parent compound are also intended for use in the systems and methods of the invention. The synthesis of such compositions may be accomplished through typical chemical modification methods such as those routinely practiced by those of ordinary skill in the art.

In still another set of embodiments, the invention encompasses the use of antisense oligonucleotides that selectively bind to regions encoding enzymes present within the fatty acid metabolism pathway, such as 2,4-dienoyl-CoA reductase or 2,4-dienoyl-CoA isomerase. Thus, a fatty acid metabolism inhibitor, in one embodiment, is an antisense oligonucleotide.

The invention, in yet another set of embodiments, includes the use of a dominant negative plasma membrane polypeptide as a fatty acid metabolism inhibitor. The end result of the use (e.g., expression) of a dominant negative polypeptide in a cell may be a reduction in functional enzymes present within the fatty acid metabolism pathway. One of ordinary skill in the art can assess the potential for a dominant negative variant of a protein or enzyme, and use standard mutagenesis techniques to create one or more dominant negative variant polypeptides. For example, one of ordinary skill in the art can modify the sequence of an enzyme coding region by site-specific mutagenesis, scanning mutagenesis, partial gene deletion or truncation, and the like. See, e.g., U.S. Pat. No. 5,580,723 and Sambrook, et al., *Molecular Cloning: A Laboratory Manual*, Second Edition, Cold Spring Harbor Laboratory Press, 1989. One of ordinary skill in the art then can test the population of mutagenized polypeptides for diminution in a selected and/or for retention of such activity of the protein or enzyme. Other similar methods for creating and testing dominant negative variants of a protein will be apparent to one of ordinary skill in the art.

Glycolytic Inhibitor

Preferred glycolytic inhibitors are 2-deoxyglucose compounds, defined herein as homologs, analogs, and/or derivatives of 2-deoxy-D-glucose. While the levo form is not prevalent, and 2-deoxy-D-glucose is preferred, the term "2-deoxyglucose" is intended to cover inter alia either 2-deoxy-D-glucose and 2-deoxy-L-glucose, or a mixture thereof. In general glycolytic inhibitors can have the formula:

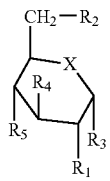

wherein: X represents an O or S atom; $R_1$ represents a hydrogen atom or a halogen atom; $R_2$ represents a hydroxyl group, a halogen atom, a thiol group, or CO—$R_6$; and $R_3$, $R_4$, and $R_5$ each represent a hydroxyl group, a halogen atom, or CO—$R_6$, wherein $R_6$ represents an alkyl group of from 1 to 20 carbon atoms, and wherein at least two of $R_3$, $R_4$, and $R_5$ are hydroxyl groups. The halogen atom is as described above with respect to the oxirane carboxylic acid compounds, and in $R_2$, $R_3$, $R_4$, and $R_5$. The halogen atom is preferably F, and $R_6$ is preferably a $C_3$-$C_{15}$ alkyl group.

Examples of 2-deoxyglucose compounds useful in the invention are: 2-deoxy-D-glucose, 2-deoxy-L-glucose; 2-bromo-D-glucose, 2-fluoro-D-glucose, 2-iodo-D-glucose, 6-fluoro-D-glucose, 6-thio-D-glucose, 7-glucosyl fluoride, 3-fluoro-D-glucose, 4-fluoro-D-glucose, 1-O-propyl ester of 2-deoxy-D-glucose, 1-O-tridecyl ester of 2-deoxy-D-glucose, 1-O-pentadecyl ester of 2-deoxy-D-glucose, 3-O-propyl ester of 2-deoxy-D-glucose, 3-O-tridecyl ester of 2-deoxy-D-glucose, 3-O-pentadecyl ester of 2-deoxy-D-glucose, 4-O-propyl ester of 2-deoxy-D-glucose, 4-O-tridecyl ester of 2-deoxy-D-glucose, 4-O-pentadecyl ester of 2-deoxy-D-glucose, 6-O-propyl ester of 2-deoxy-D-glucose, 6-O-tridecyl ester of 2-deoxy-D-glucose, 6-O-pentadecyl ester of 2-deoxy-D-glucose, and 5-thio-D-glucose, and mixtures thereof.

A preferred glycolytic inhibitor is 2-deoxy-D-glucose, which has the structure:

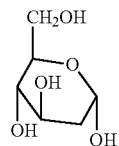

UCP and/or Fas Antibody

The target antigens for antibodies useful in this invention are UCP and/or Fas antigens. By "Fas" is meant CD95, which is a molecule well characterized as a death-inducing receptor ("Fas" does not refer to fatty acid synthase, which is usually designated as "FAS"). UCP and Fas antibodies are available from commercial sources as intact functional antibodies, e.g., as described above. As used herein, the term "antibody" means not only intact antibody molecules but also fragments of antibody molecules retaining specific binding ability. Such fragments are also well known in the art and are regularly employed both in vitro and in vivo. In particular, as used herein, the term "antibody" means not only intact immunoglobulin molecules but also the well-known active fragments $F(ab')_2$, and Fab. $F(ab')_2$, and Fab fragments which lack the Fc fragment of intact antibody, clear more rapidly from the circulation, and may have less non-specific tissue binding of an intact antibody (Wahl, et al., *J. Nucl. Med.* 24:316-325, 1983).

As is well known in the art, the complementarity determining regions (CDRs) of an antibody are the portions of the antibody that are largely responsible for antibody specificity. The CDRs directly interact with the epitope of the antigen. In both the heavy chain and the light chain variable regions of IgG immunoglobulins, there are four framework regions (FR1 through FR4) separated respectively by three complementarity-determining regions (CDR1 through CDR3). The framework regions (FRs) maintain the tertiary structure of the paratope, which is the portion of the antibody involved in the interaction with the antigen. The CDRs, and in particular the CDR3 regions, and more particularly the heavy chain CDR3, each can contribute to antibody specificity. Because these CDR regions and, in particular, the CDR3 region may confer antigen specificity on the antibody, these regions may be incorporated into other antibodies or peptides, e.g., to confer the identical specificity onto that antibody or peptide.

Many UCP antibodies are commercially available. These include, but are not limited to, those antibodies commercially available from SANTA CRUZ BIOTECHNOLOGY®, INC. e.g. UCP1 (m-17, sc-6529), UCP1 (C-17, sc-6528), UCP2 (A19, sc-6527), UCP2 (N19, sc-6526), UCP2 (c-20, sc-6525, and UCP3 (C-20, sc-7756); antibodies commercially available from Research Diagnostics, Inc., e.g., goat anti-UCP1 human/mouse/rat (RDI-UCP1 Cabg); goat anti-UCP1 human/mouse/rat (RDI-MUCP1 Cabg); goat anti-UCP2 human/mouse/rat (RDI-UCP2Nabg); goat anti-UCP2 human/mouse/rat (RDI-UCP2Cabg); goat anti-UCP2 human/mouse/rat (RDI-UCP2C1abg); rabbit anti-murine UCP1 (RDI-MUCP12abrX); rabbit anti-murine UCP1 (RDI-MUCP19abrX); rabbit anti-murine UCP2 (RDI-MUCP2abrX); rabbit anti-murine UCP2 (RDI-MUCP2CabrX); rabbit anti-human UCP2 (RDI-UCP2MabrX); UCP3L (see Boss, et al. *FEBS Lett.*, 408:38-

42, 1997; Vidal-Plug et al., *Biochem Biophys. Res. Comm.*, 235:79-82, 1997); rabbit anti-human UCP3 (RDI-UCP3abrX); rabbit anti-human UCP3 (RDI-UCP3CbrX); rabbit anti-human UCP3 (RDI-UCP3MabrX); rabbit anti-rat UCP3 (RDI-RTUCP3MabrX), etc.

Many Fas antibodies are commercially available. These include but are not limited to those antibodies commercially available from: Rabbit polyclonal Fas antibody (ab2437) (abcam); Rabbit Anti-Human FAS Ligand Antibody Polyclonal Antibody, (Alpha Diagnostic International Inc); Mouse Anti-CD178 (Fas Ligand) Monoclonal Antibody, Clone 33 (BD Biosciences Pharmingen); Mouse Anti-Fas Monoclonal Antibody, Clone G254-274 (BD Biosciences Pharmingen;) Mouse Anti-Fas Ligand Monoclonal Antibody, Clone G247-4 (BD Biosciences Pharmingen); Mouse Anti-Fas Ligand Monoclonal Antibody, Clone NOK-2 (BD Biosciences Pharmingen); Hamster Anti-Human CD178 (Fas Ligand) Monoclonal Antibody, Biotin Labeled, Clone 4H9 (Beckman Coulter); Hamster Anti-Human CD178 (Fas Ligand) Monoclonal Antibody, Clone 4A5 (Beckman Coulter); Mouse Anti-Human CD95 (APO-1; Fas; TNF receptor family) Monoclonal Antibody, FITC Labeled, Clone UB2 (Beckman Coulter); Mouse Anti-Human CD95 (APO-1; Fas; TNF receptor family) Monoclonal Antibody, Phycoerythrin Labeled, Clone UB2 (Beckman Coulter); Mouse Anti-Human CD95 (APO-1; Fas; TNF receptor family) Monoclonal Antibody, Phycoerythrin Labeled, Clone 7C11 (Beckman Coulter); Mouse Anti-Human CD95 (APO-1; Fas; TNF receptor family) Monoclonal Antibody, Clone ZB4 (Beckman Coulter); Mouse Anti-Human CD95 (APO-1; Fas; TNF receptor family) Monoclonal Antibody, Clone CH11 (Beckman Coulter) Mouse Anti-Human CD95 (APO-1; Fas; TNF receptor family) Monoclonal Antibody, Clone UB2 (Beckman Coulter) Mouse Anti-Human CD95 (APO-1; Fas; TNF receptor family) Monoclonal Antibody, Clone 7C11 (Beckman Coulter) Mouse Anti-Human Fas/CD95/Apo-1 Monoclonal Antibody, Clone B-G27 (BioSource International); Anti-Human APO-1/Fas Antibody, (CalTag); Mouse Anti-Human CD95L (Fas ligand) Antibody (CalTag); Anti-Human Fas Ligand Antibody (CalTag); Mouse Anti-Fas (CD95/APO-1) Monoclonal Antibody, Labeled or Unconjugated, Clone B-G27, Clone B-D29, Clone ICO-160, Clone SM1/1, Clone SM1/23, Clone 95C02, Clone FSL01 (CHEMICON); Rabbit Anti-Human FAS (APO-1, CD95) Polyclonal Antibody, Unconjugated (Delta Biolabs); Anti-Human CD95 (Fas/APO-1) Antibody, (eBioscience); Rabbit Anti-CD95 (Fas) Ab-4 Polyclonal Antibody (Lab Vision); Mouse Anti-CD95 (Fas) Ab-3 Monoclonal Antibody (Lab Vision); Mouse Anti-CD95 (Fas) Ab-2 Monoclonal Antibody, Clone 95C02 (Lab Vision); Rabbit Anti-Human CD95 (Fas) Ab-5, Epitope Specific Antibody, (Lab Vision); Rabbit Anti-FADD (FAS-Associated Death Domain-containing Protein) Ab-1 Polyclonal Antibody (Lab Vision); Rabbit Anti-Mouse FADD (FAS-Associated Death Domain-containing Protein) Ab-2 Polyclonal Antibody (Lab Vision); Mouse Anti-Human FAP-1 (Fas associated phosphatase-1) Ab-1 Monoclonal Antibody, Clone 2C8 (Lab Vision); Mouse Anti-Fas Ligand Ab-1 Monoclonal Antibody (Lab Vision); Rabbit Anti-Human Fas Ligand Epitope Specific Antibody, (Lab Vision); Anti-Human Fas-Associated Death Domain Protein (FADD) Monoclonal Antibody, Unconjugated, Clone 1F7 (Leinco Technologies, Inc.); Mouse Anti-Human Fas (Apo-1; CD95) Monoclonal Antibody, Clone LT95 (Novus Biologicals); Rabbit Anti-Human Fas antigen Polyclonal Antibody, (Novus Biologicals); Mouse Anti-Human Fas antigen Monoclonal Antibody, Clone LOB 3/17 (Novus Biologicals); Mouse Anti-Human FAS Intracellular Fragment Monoclonal Antibody, Clone GH-9 (Novus Biologicals); Goat Anti-Human Fas-L (Fas Ligand) Polyclonal Antibody, (PeproTech); Mouse Anti-Human CD95/Fas Monoclonal Antibody, Clone DX-2, Clone DX-3 (SouthernBiotech); Mouse Anti-Fas Monoclonal Antibody, Clone UB2, Clone ZB4 (Stressgen Bioreagents); Mouse Anti-Human CD178 FAS Ligand (CD951) Monoclonal Antibody, (United States Biological); Rabbit Anti-Human FADD (Fas-Associated Death Domain Protein, MORT1) Polyclonal Antibody, (United States Biological); Mouse Anti-Human Fas (CD95, APO-1) Monoclonal Antibody, (United States Biological); Hamster Anti-Human Fas (CD95, APO-1) Monoclonal Antibody, (United States Biological); Mouse Anti-Human Fas, Intracellular Fragment Monoclonal Antibody, (United States Biological); Mouse Anti-Human Fas, Neutralizing (CD95, APO-1) Monoclonal Antibody, (United States Biological); Mouse Anti-Human Fas Activating Monoclonal Antibody, (Upstate); Mouse Anti-Human Fas Neutralizing Monoclonal Antibody, (Upstate); Mouse Anti-Human Fas Ligand Monoclonal Antibody, (Upstate).

According to one embodiment of the invention, the UCP and/or Fas antibody is an intact soluble monoclonal antibody in an isolated form or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains can be further divided into subregions referred to as variable regions and constant regions. As used herein, the term "monoclonal antibody" refers to a homogenous population of immunoglobulins that specifically bind to an epitope (i.e. antigenic determinant), e.g., of a plasma membrane UCP and/or Fas.

The monoclonal antibody, in some cases, may be an intact humanized a monoclonal antibody. A "humanized monoclonal antibody," as used herein, is a human monoclonal antibody (or functionally active fragment thereof) having human constant regions and a binding CDR3 region from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs, and optionally some of the framework regions, may be covalently joined to human FR and/or Fc/pFc' regions to produce a functional antibody. There are entities that will synthesize humanized antibodies from specific murine antibody regions commercially, such as Protein Design Labs (Mountain View, Calif.).

European Patent Publication No. 0239400 (from European Patent Application No. 87302620.7, filed Mar. 26, 1987), the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector, including a suitable promoter operably linked to a DNA sequence encoding at least a variable domain of an Ig heavy or light chain, and the variable domain comprising framework regions from a human antibody and a CDR region of a murine antibody, is prepared. Optionally, a second replicable expression vector is prepared, which includes a suitable promoter operably linked to a DNA sequence encoding at least the variable domain of a complementary human Ig light or heavy chain, respectively. A cell line is then transformed with the vectors. In some cases, the cell line is an immortalized mammalian cell line of lymphoid origin, such as a myeloma, hybridoma, trioma, or quadroma cell line, or is a normal lymphoid cell that has been immortalized by transformation with a virus. The transformed cell line is then cultured under conditions known to those of ordinary skill in the art to produce the humanized antibody.

As set forth in European Patent Application 0239400, several techniques are well known in the art for creating the particular antibody domains to be inserted into the replicable vector. For example, the DNA sequence encoding the domain may be prepared by oligonucleotide synthesis. Alternatively, a synthetic gene lacking the CDR regions in which four framework regions are fused together with suitable restriction sites at the junctions, such that double stranded synthetic or restricted subcloned CDR cassettes with sticky ends could be ligated at the junctions of the framework regions, can be prepared. Another method involves the preparation of the DNA sequence encoding the variable CDR containing domain by oligonucleotide site-directed mutagenesis. Each of these methods is well known in the art. Those of ordinary skill in the art may thus be able to construct humanized antibodies containing a murine CDR region, without destroying the specificity of the antibody for its epitope.

Human monoclonal antibodies may be made by any of the methods known in the art, such as those disclosed in U.S. Pat. No. 5,567,610; U.S. Pat. No. 5,565,354; U.S. Pat. No. 5,571,893; Kozber, *J. Immunol.*, 133: 3001, 1984; Brodeur, et al., *Monoclonal Antibody Production Techniques and Applications*, p. 51-63, Marcel Dekker, Inc., 1987; and Boerner, et al., *J. Immunol.*, 147:86-95, 1991. In addition to the conventional methods for preparing human monoclonal antibodies, such antibodies may also be prepared by immunizing transgenic animals that are capable of producing human antibodies (e.g., Jakobovits, et al., *Proc. Natl. Acad. Sci. USA*, 90: 2551, 1993; Jakobovits, et al., *Nature*, 362:255-258, 1993; Bruggermann, et al., *Year in Immunol.*, 7:33, 1993; and U.S. Pat. No. 5,569,825.

The UCP and/or Fas binding peptides may also be functionally active antibody fragments in some cases. For instance, only a small portion of an antibody molecule, the paratope, is often involved in the binding of the antibody to its epitope (see, in general, Clark, *The Experimental Foundations of Modern Immunology*, Wiley & Sons, Inc., 1986; Roitt, *Essential Immunology*, 7th Ed., Blackwell Scientific Publications, 1991). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is often referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation. The terms Fab, Fc, pFc', F(ab')$_2$ and Fv are used consistently with their standard immunological meanings. See, e.g., Klein, *Immunology*, John Wiley, 1982; Clark, *The Experimental Foundations of Modern Immunology*, Wiley & Sons, Inc., 1986; Roitt, *Essential Immunology*, 7th Ed., Blackwell Scientific Publications, 1991.

EXAMPLES

The following examples will further illustrate the invention.

Materials and Methods

Cell Culture

All cell lines were cultured in RPMI 1640 culture medium. The medium is supplemented with 5% fetal bovine serum (FBS), 2 mM L-Glutamine, 500 units/mL pennicillin/500 µg/mL of streptomycin, 10 mM HEPES Buffer, $10^{-5}$M 2-mercaptoethanol (2-ME), 1 mM MEM Sodium Pyruvate, and 0.04 µg/mL of Gentamicin (All reagents from Gibco BRL). Cells were maintained at 37° C. in a humidified atmosphere under 5% $CO_2$ in air.

Cell Counting

Cells were harvested and resuspended in 1 mL of RPMI medium. A 1:20 dilution of the cell suspension was made by using 50 µL of trypan blue (Sigma chemicals), 45 µL of Phosphate Buffered Saline (PBS) supplemented with 2.5% FBS, and 5 µL of the cell suspension. Live cells were counted using a hemacytometer and the following calculation was used to determine cell number: Average # of Cells×Dilution× $10^4$.

Preparation of Cell for Staining

For staining protocols, between $0.5 \times 10^6$ and $1.0 \times 10^6$ cells were used; all staining was done in a 96-well U-bottom staining plate. Cells were harvested by centrifugation for 5 minutes at 300×g, washed with PBS/2.5% FBS, and resuspended into PBS/2% FBS for staining. Cells were plated into wells of a labeled 96-well plate in 100 µL of PBS/2.5% FBS.

Flow Cytometry

Once samples had been prepared and transferred into flow cytometric tubes, they were analyzed on a Becton/Dickinson Flow Cytometer. For antibodies that are PE conjugated and for MITOTRACKER® Red, a program for red colored fluorochromes was utilized. For antibodies that are FITC conjugated and for DCFda, LYSOSENSOR™, and LYSOTRACKER™ a program for green colored fluorochromes was used.

Dot Plots as a Function of Live Versus Dead Cells

The cells were cultured at a concentration of 0.5 to 1 million cells per ml. Cells were untreated or treated with etomoxir or 2-deoxy-D-glucose at a concentration of 2.5 mM at the indicated concentrations for either 24 or 48 hours. In additional experiments, under each of these culture conditions, the cells were cultured for 24 hours at which time point, polyclonal anti-UCP-2 was added at a 1:1000 dilution of stock provided by Alpha Diagnostics, San Antonio, Tex. Cells were harvested and analyzed by flow cytometry. Each dot on the dot plots of FIGS. 1, 3, 5, 7, 9, and 11 represents one cell. Five thousand cells were assessed for forward scatter (FS), as a function of cell size, versus side scatter (SS), as a function of cellular granularity. The upper ellipse represents live cells by these criterion and the lower ellipse in each dot plot represents the dead cells.

Statistical Analysis, Percents

Percents: Gating is a tool provided by CELLQUEST™ software and allows for the analysis of a certain population of cells. Gating around both the live and dead cell populations gave a percent of the cell numbers that was in each population. After the gates were drawn, a percent value of dead cells, as shown in FIGS. 2, 4, 6, 8, 10, and 12, was calculated by taking the number of dead cells divided by the number of total cells and multiplying by one hundred.

Tumor Implantation

Mice were purchased from the Animal Production Program of National Cancer Institute, Frederick, Md. The animals used were Athymic Ncr-nu/nu (strain code 01B74). HL60 MDR cells were harvested and reconstituted at 1 million cells per 100 microliters of phosphate buffered saline. One million tumor cells per injection site were implanted subcutaneously on two sites of the animal's back. Treatments began at exactly seven days post tumor implantation. Tumor size/volume was monitored twice weekly using measurement calipers, with the formula Tumor Volume=$\pi \times$(short diameter)$^2 \times$(long diameter)/6.

Treatments

Treatment groups were: etomoxir at 200 micrograms/day; 2-deoxy-D-glucose at 2.5 mM in 100 microliters daily; and the combination daily of etomoxir at 200 micrograms and 2-deoxy-D-glucose at 2.5 mM in 100 microliters.

Example 1

Figure 2:
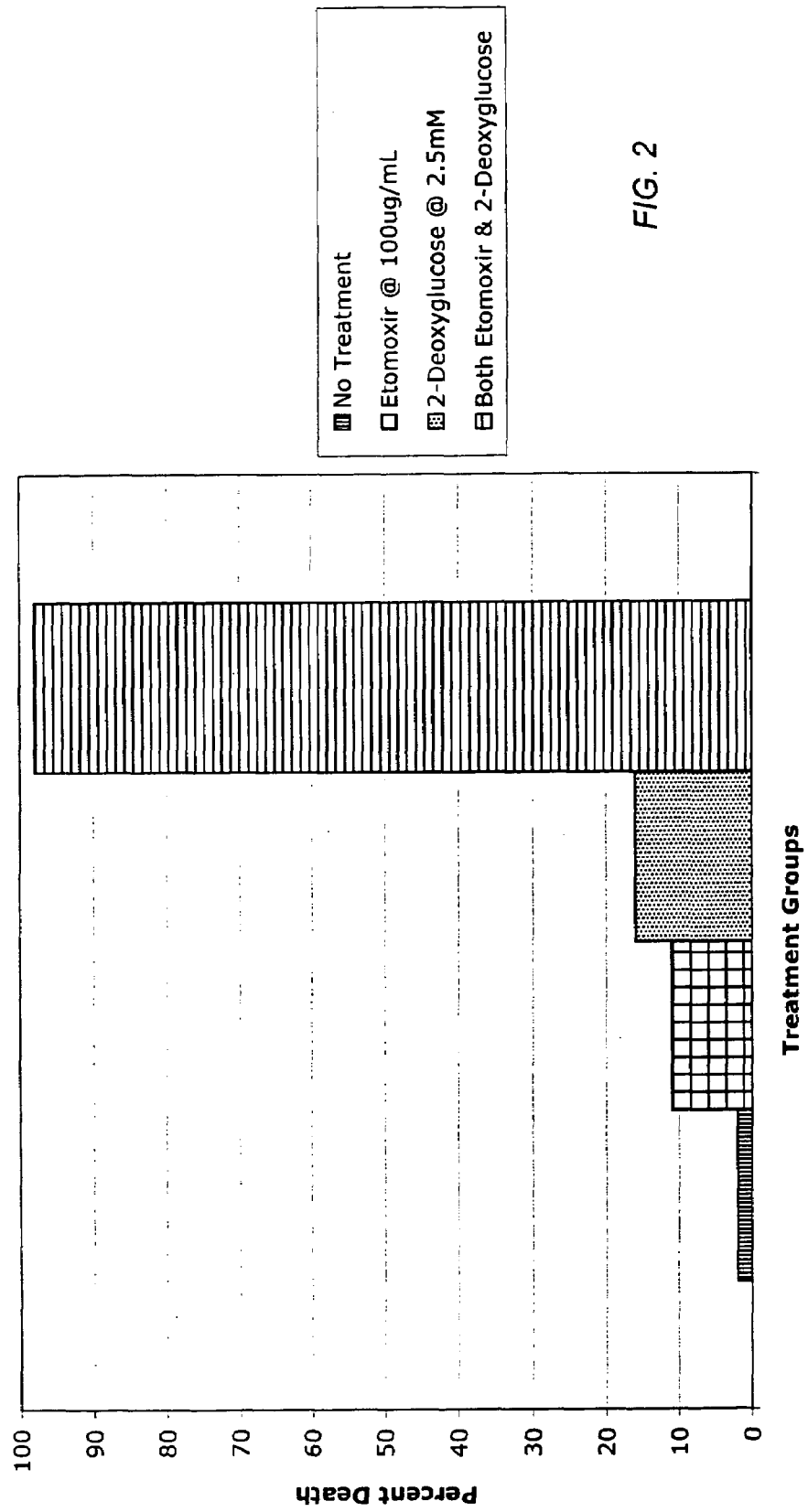
FIG. 2 shows the percent death of HL60 MDR cells untreated or treated for 24 hours with etomoxir, 2-deoxy-D-glucose, or both, at the indicated concentrations.

HL60 MDR human leukemia cells were cultured as described above under "Materials and Methods". Cells were untreated or treated with etomoxir, with 2-deoxy-D-glucose, or with a combination of etomoxir and 2-deoxy-D-glucose, at concentrations indicated in FIG. 1 for 24 hours. Cells were harvested and analyzed by flow cytometry. Dot plots are shown in FIG. 1 as functions of live versus dead cells, as described above under "Materials and Methods"—"Dot plots as a function of live versus dead cells". FIG. 2 shows the percent death of the HL60 MDR cells, calculated as described above under "Materials and Methods"—"Statistical Analysis, Percents." The percent of cell deaths for HL60 MDR cells after 24 hours was: (a) 2% when untreated, (b) 11% when treated with etomoxir alone, (c) 16% when treated with 2-deoxy-D-glucose alone, and (d) 98% when treated with the combination of etomoxir and 2-deoxy-D-glucose. Thus the combination of glycolytic inhibitor and fatty acid metabolism inhibitor had a dramatically synergistic effect in killing the multi drug resistant HL60 MDR human leukemia cells.

Example 2

Figure 4:
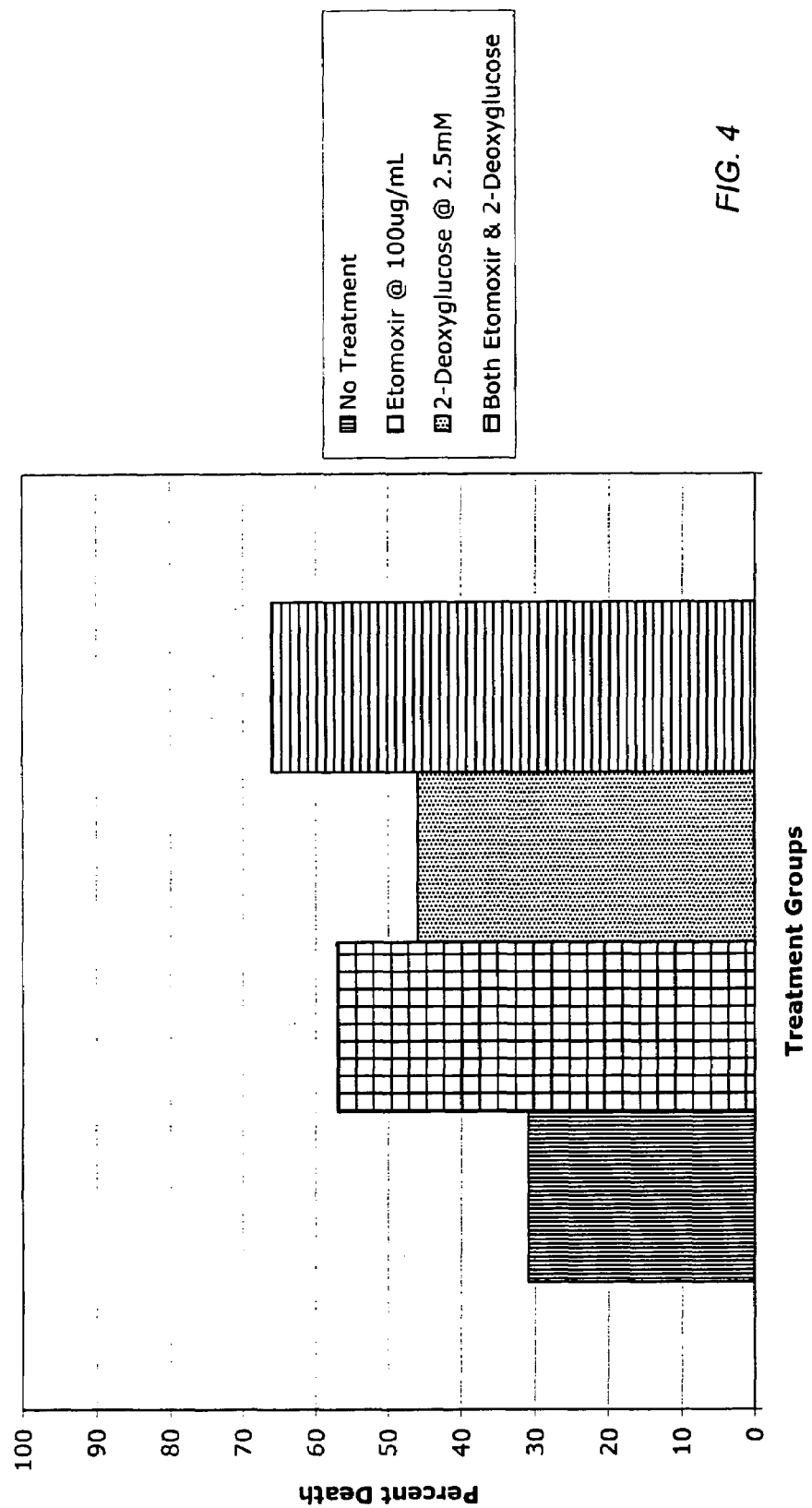
FIG. 4 shows the percent death of RD cells untreated or treated for 24 hours with etomoxir, 2-deoxy-D-glucose, or both, at the indicated concentrations.

Referring to FIGS. 3 and 4, RD cells (rhabdomyosarcoma cells—not drug resistant), cultured as described above under "Materials and Methods" were untreated or treated with etomoxir, with 2-deoxy-D-glucose, or with a combination of etomoxir and 2-deoxy-D-glucose, at concentrations indicated in FIG. 3 for 24 hours. Cells were harvested and analyzed by flow cytometry. Dot plots are shown in FIG. 3. FIG. 4 shows the percent death of the RD cells. The percent of cell deaths for RD cells after 24 hours was: (a) 31% when untreated, (b) 57% when treated with etomoxir alone, (c) 46% when treated with 2-deoxy-D-glucose alone, and (d) 66% when treated with the combination of etomoxir and 2-deoxy-D-glucose. The combination of glycolytic inhibitor and fatty acid metabolism inhibitor still had a synergistic effect in killing the RD cells but not nearly as much as with the multi drug resistant cells in Example 1.

Example 3

Figure 5:
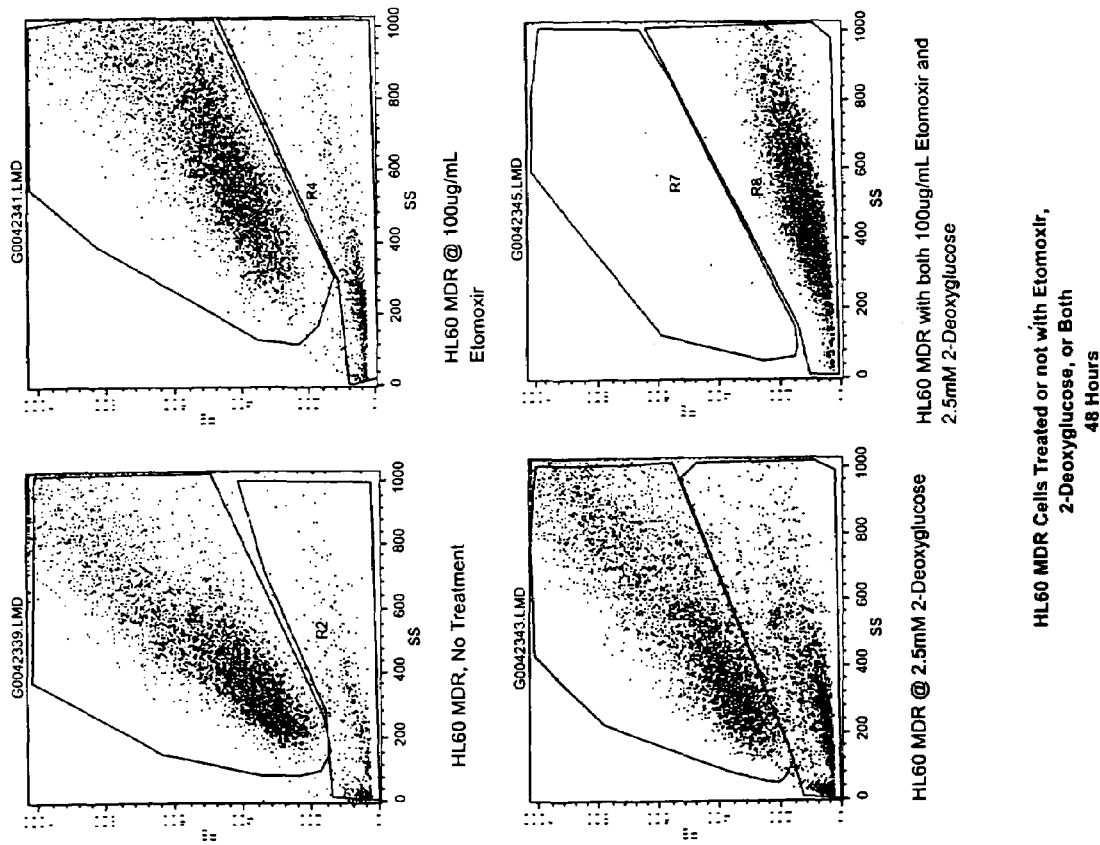
FIG. 5 is a dot plot as a function of live versus dead HL60 MDR cells untreated or treated with etomoxir, 2-deoxy-D-glucose, or both, at the indicated concentrations for 48 hours.
Figure 6:
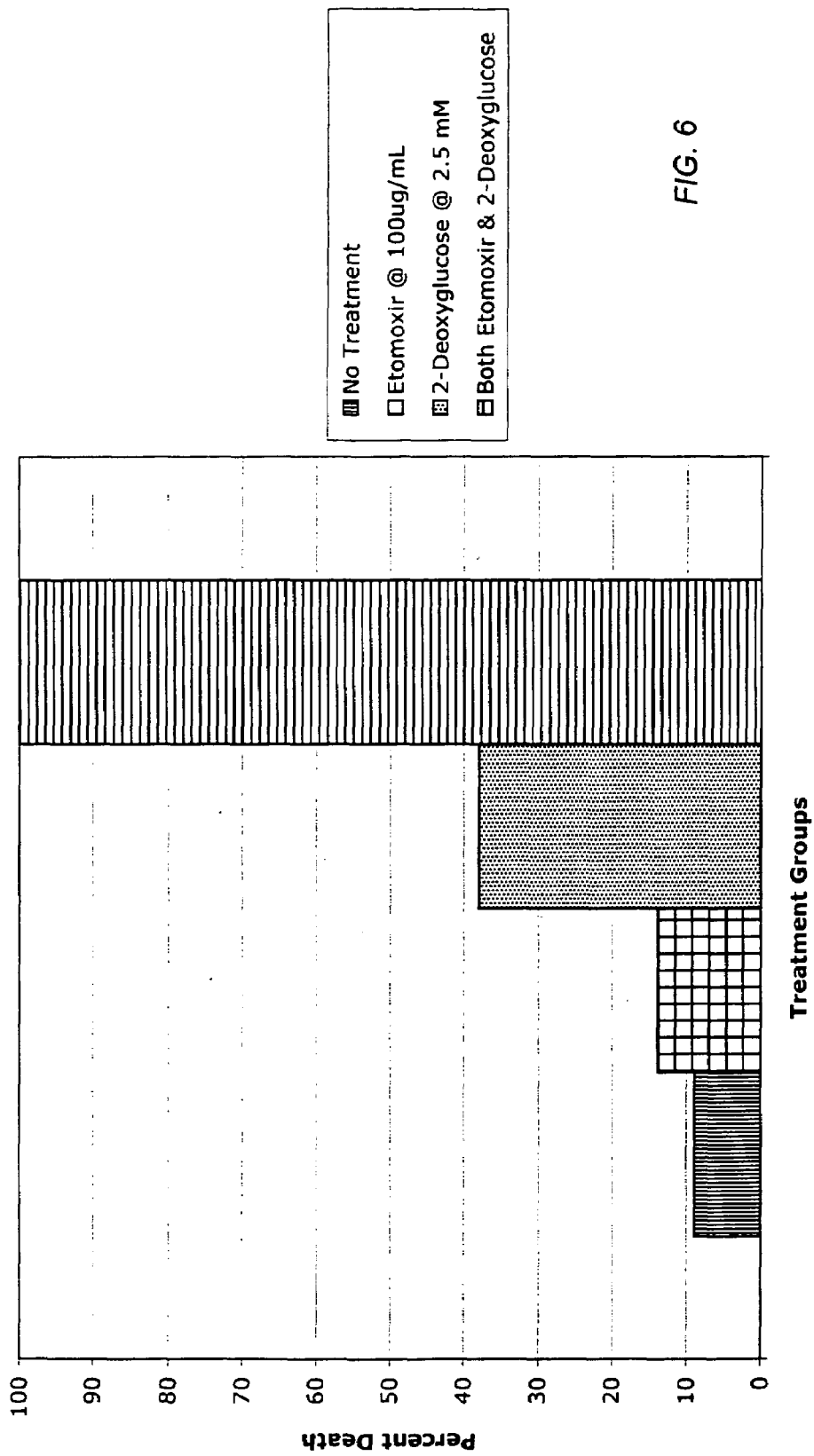
FIG. 6 shows the percent death of HL60 MDR cells untreated or treated for 48 hours with etomoxir, 2-deoxy-D-glucose, or both, at the indicated concentrations.

Referring to FIGS. 5 and 6, HL60 MDR cells, cultured as described in Example 1, were untreated or treated with etomoxir, with 2-deoxy-D-glucose, or with a combination of etomoxir and 2-deoxy-D-glucose, at concentrations indicated in FIG. 5 for 48 hours. Cells were harvested and analyzed by flow cytometry. Dot plots are shown in FIG. 5. FIG. 6 shows the percent death of the HL60 cells. The percent of cell deaths for HL60 MDR cells after 48 hours was: (a) 9% when untreated, (b) 14% when treated with etomoxir alone, (c) 38% when treated with 2-deoxy-D-glucose alone, and (d) 100% when treated with the combination of etomoxir and 2-deoxy-D-glucose. Thus, increasing exposure time increased cell deaths generally, but most dramatically with the combination of glycolytic inhibitor and fatty acid metabolism inhibitor, where 100% of the HL60 MDR cells were killed.

Example 4

Figure 8:
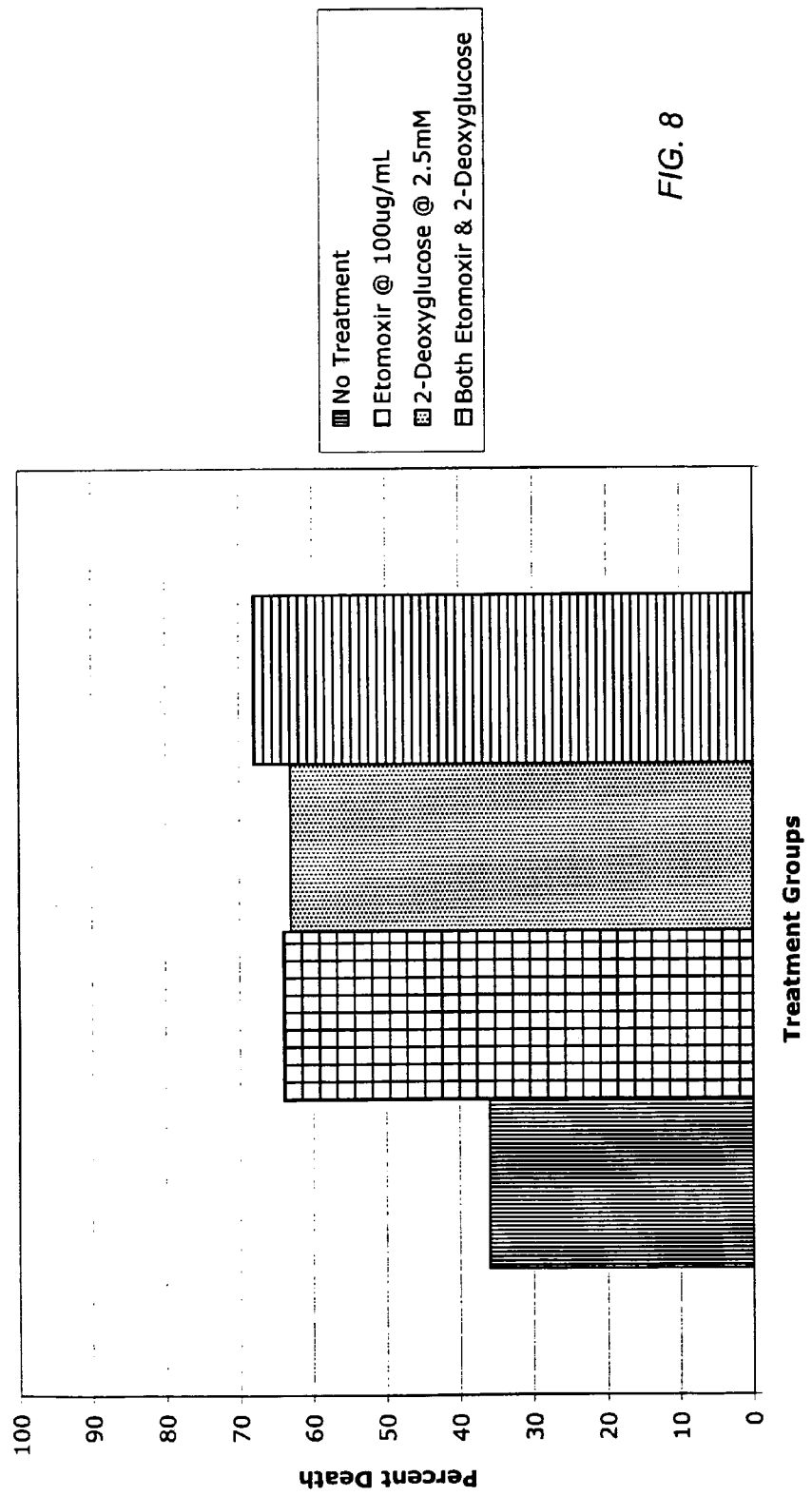
FIG. 8 shows the percent death of RD cells untreated or treated for 48 hours with etomoxir, 2-deoxy-D-glucose, or both, at the indicated concentrations.

Referring to FIGS. 7 and 8, RD cells, cultured as described in Example 2, were untreated or treated with etomoxir, with 2-deoxy-D-glucose, or with a combination of etomoxir and 2-deoxy-D-glucose, at concentrations indicated in FIG. 7 for 48 hours. Cells were harvested and analyzed by flow cytometry. Dot plots are shown in FIG. 7. FIG. 8 shows the percent death of the RD cells. The percent of cell deaths for RD cells after 48 hours was: (a) 36% when untreated, (b) 64% when treated with etomoxir alone, (c) 63% when treated with 2-deoxy-D-glucose alone, and (d) 68% when treated with the combination of etomoxir and 2-deoxy-D-glucose. Increasing the treatment time for RD cells only modestly increased the number of cells killed.

Example 5

Figure 10:
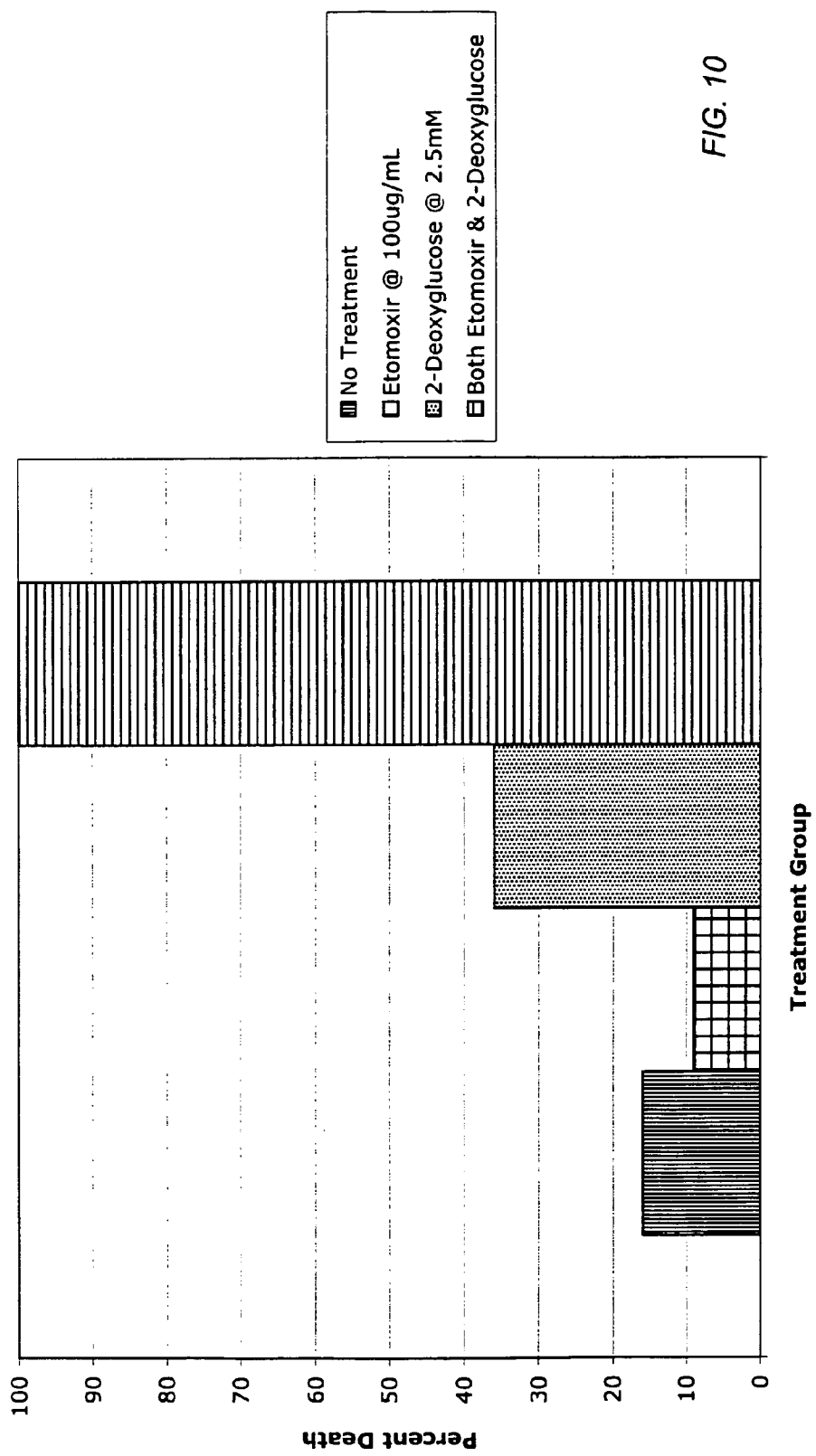
FIG. 10. shows the percent death of HL60 MDR cells treated for 48 hours with anti-UCP2 antibody and otherwise untreated or treated with etomoxir, 2-deoxy-D-glucose, or both, at the indicated concentrations.

Referring to FIGS. 9 and 10, HL60 MDR cells, cultured as described in Example 1, were treated with anti-UCP2 antibody and otherwise untreated or treated simultaneously with etomoxir, 2-deoxy-D-glucose, or both, at concentrations indicated in FIG. 9 for 48 hours. Cells were harvested and analyzed by flow cytometry. Dot plots are shown in FIG. 9. FIG. 10 shows the percent death of the HL60 cells. The percent of cell deaths for HL60 MDR cells after 48 hours was: (a) 16% when treated only with the antibody, (b) 9% when treated with the antibody and etomoxir, (c) 36% when treated with the antibody and 2-deoxy-D-glucose alone, and (d) 100% when treated with the combination of antibody, etomoxir and 2-deoxy-D-glucose. Thus, treatment with the antibody had a minor effect when the cells were otherwise untreated, but otherwise little effect, a result that is attributed to the fact that it was administered at the same time as the etomoxir. As shown in this example and in Example 3, the combination of glycolytic inhibitor and fatty acid metabolism inhibitor resulted in a 100% kill rate with or without the antibody.

Example 6

Figure 12:
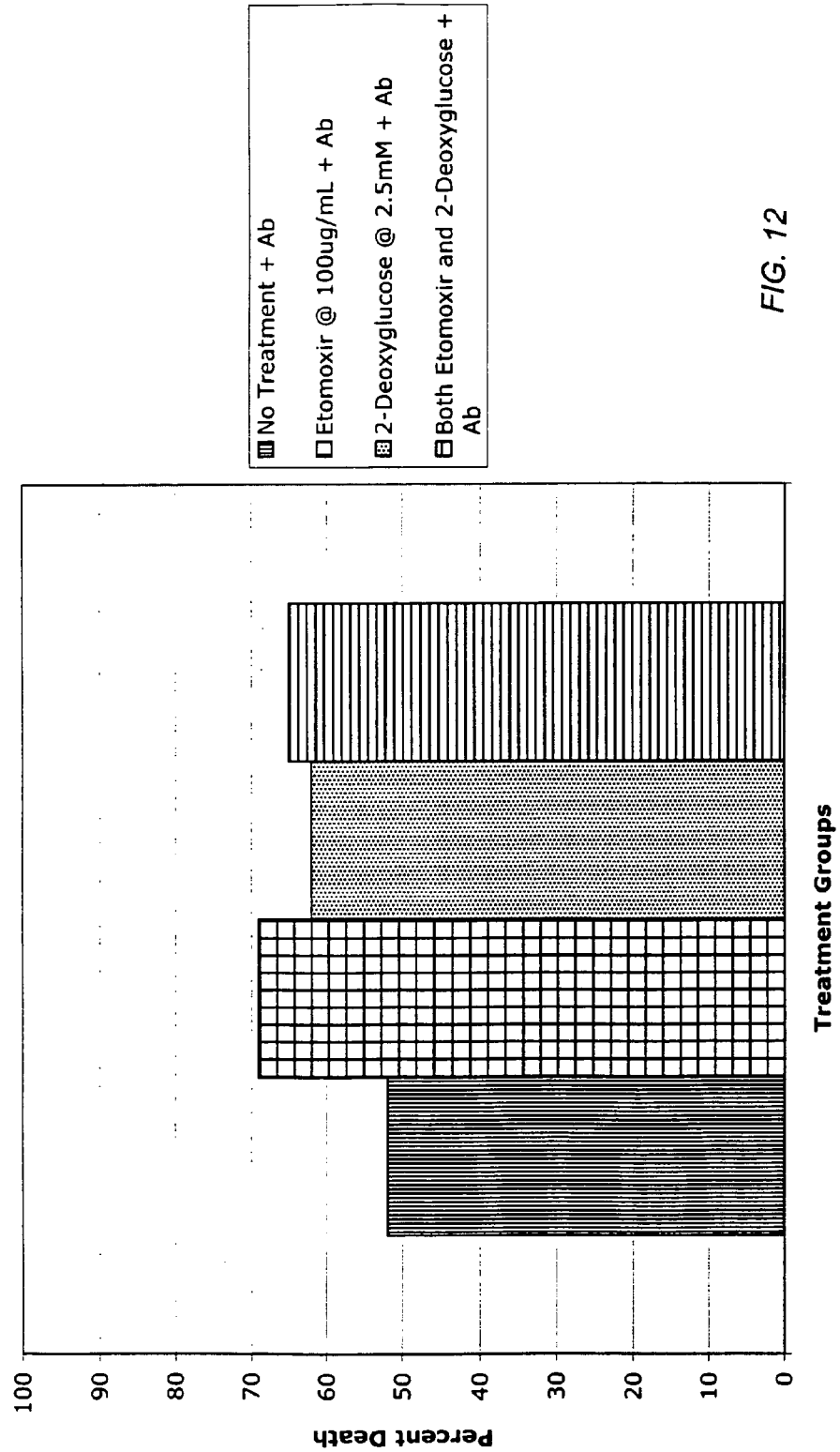
FIG. 12 shows the percent death of RD cells treated for 48 hours with anti-UCP2 antibody and otherwise untreated or treated with etomoxir, 2-deoxy-D-glucose, or both, at the indicated concentrations.

Referring to FIGS. 11 and 12, RD cells, cultured as described in Example 2, were treated with anti-UCP2 antibody and otherwise untreated or treated simultaneously with etomoxir, 2-deoxy-D-glucose, or both, at concentrations indicated in FIG. 11 for 48 hours. Cells were harvested and analyzed by flow cytometry. Dot plots are shown in FIG. 11. FIG. 12 shows the percent death of the RD cells. The percent of cell deaths for RD cells after 48 hours was: (a) 52% when treated only with the antibody, (b) 69% when treated with the antibody and etomoxir, (c) 62% when treated with the antibody and 2-deoxy-D-glucose alone, and (d) 65% when treated with the combination of antibody, etomoxir and 2-deoxy-D-glucose. Treatment of the RD cells with the antibody had some effect when the cells were otherwise untreated, but otherwise, as in Example 5, had little effect Example 7

HL60 MDR human leukemia cells were cultured and implanted in nude mice as described above under "Materials and Methods". The mice were given 200 ug of Etomoxir, 2.5 mM 2-Deoxy-D-glucose, or both 200 ug of Etomoxir and 2.5 mM 2-Deoxy-D-glucose given daily by IP injection. Treatment began exactly one week after tumor implantation. Tumor growth was observed for 21 days with tumor volume measured on days 7, 9, 15 and 21. The following shows the tumor volume in mm$^3$ for the four classes of mice over the 21 day period:

|  | Day 7 | Day 9 | Day 15 | Day 21 |
| --- | --- | --- | --- | --- |
| Control | 26 | 58.12 | 171.27 | 728.87 |
| Etomoxir only | 36 | 71.73 | 261.35 | 895.09 |
| 2-Deoxy-D-glucose only | 35 | 51.56 | 158.55 | 1,181.61 |
| Etomoxir and 2-deoxy-D-glucose | 24 | 37.72 | 99.76 | 296.83 |

Figure 13:
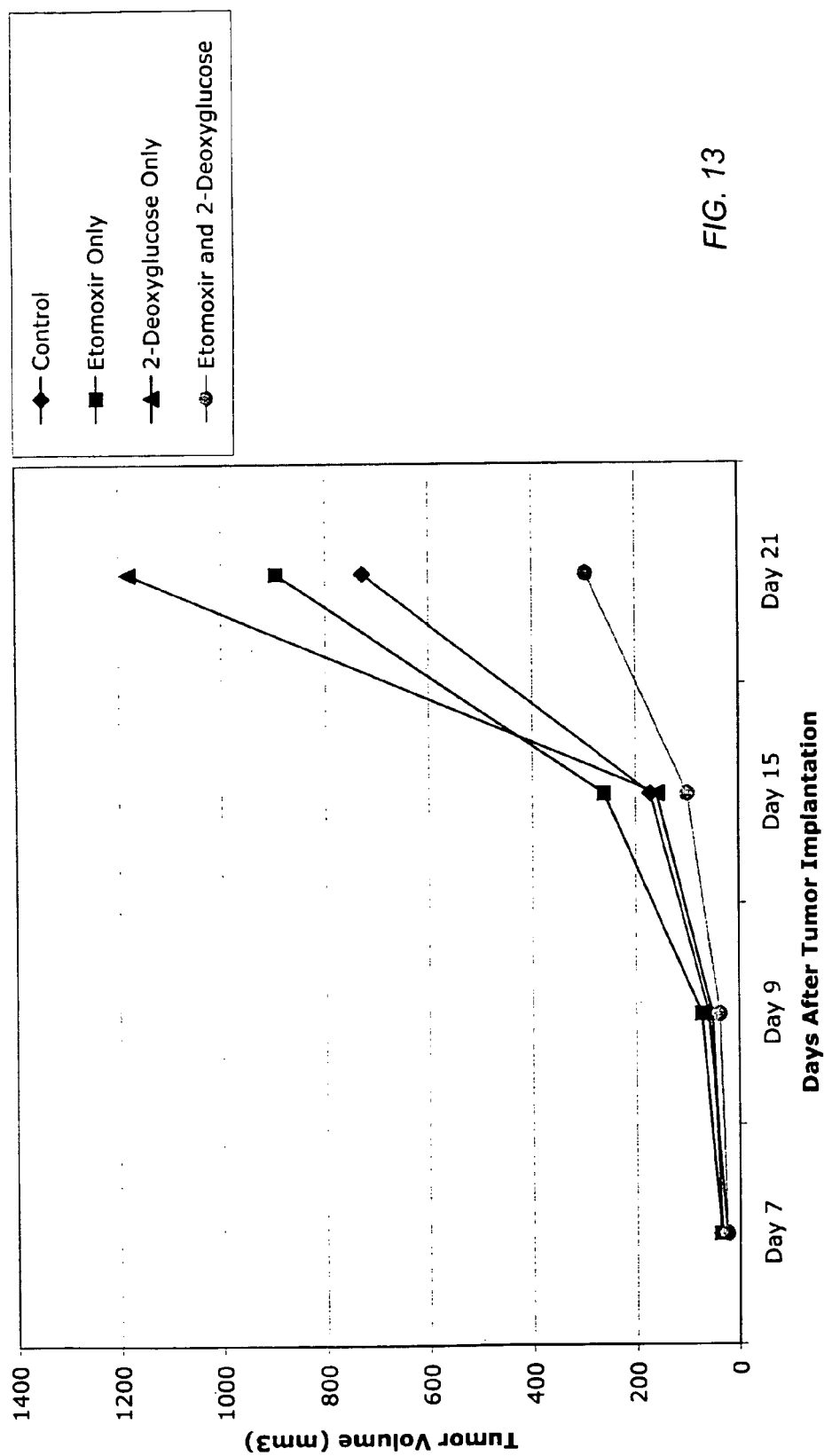
FIG. 13 shows tumor volume of an HL60 MDR tumor implanted in nude mice, treated etomoxir, 2-deoxy-D-glucose, or both, at the indicated days after tumor implantation.

FIG. 13 shows plots of the observed tumor volume over the 21 day period. The etomoxir alone and the 2-deoxy-D-glucose alone each caused an increase in tumor growth, likely because by each restricting only one of the fatty acid and glycolytic pathways, the other pathway became dominant. However, the combination of fatty acid metabolism inhibitor and glycolytic inhibitor had a dramatically synergistic effect, limiting tumor growth to 40% of the growth of the control.

In General

In one aspect, the systems and methods of the invention are useful in treating cancers, tumors, and other conditions involving rapidly dividing cell populations that are typically uncontrolled. A "rapidly dividing cell," as used herein, is a cell that is undergoing mitotic growth. Such cells are well known in the art and include, but are not limited to, tumor cells, cancer cells, lymphocytes (T cells or B cells), bacteria, and pancreatic beta (β) cells. The systems and methods are useful for inducing cell death in many types of mammalian cells, including in tumor cells. A "tumor cell," as used herein, is a cell that is undergoing unwanted mitotic proliferation. A tumor cell, when used in the in vitro aspects of the invention, can be isolated from a tumor within a subject, or may be part of an established cell line.

As used herein, the term "cell death" is used to refer to either of the processes of apoptosis or cell lysis. In both apoptosis and cell lysis, the cell dies, but the processes occur through different mechanisms and/or different metabolic states of the cell. Apoptosis is a process of cell death in which the cell undergoes shrinkage and fragmentation, followed by phagocytosis of the cell fragments. Apoptosis is well known in the art and can be assessed by any art-recognized method. For example, apoptosis can easily be determined using flow cytometry, which is able to distinguish between live and dead cells.

A tumor cell in a subject may be part of any type of cancer. Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In general, an effective amount of a composition for treating a cancer will be that amount necessary to inhibit mammalian cancer cell proliferation in situ. Those of ordinary skill in the art are well schooled in the art of evaluating effective amounts of anti-cancer agents.

In one set of embodiments, the invention includes a method of treating a subject susceptible to or exhibiting symptoms of cancer. In some cases, the cancer is drug-resistant or multi-drug resistant. As used herein, a "drug-resistant cancer" is a cancer that is resistant to conventional commonly known cancer therapies. Examples of conventional cancer therapies include treatment of the cancer with agents such as methotrexate, doxorubicin, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. A "multi-drug resistant cancer" is a cancer that resists more than one type or class of cancer agents, i.e., the cancer is able to resist a first drug having a first mechanism of action, and a second drug having a second mechanism of action. In some cases, the subject is not otherwise indicated for treatment with the inhibitor, for example, the subject is not indicated for obesity treatment.

In one aspect, any of the systems and methods of the invention described herein can be used in conjunction with one or more other forms of cancer treatment. For example, in one embodiment, a fatty acid metabolism inhibitor and/or a glycolytic inhibitor and/or UCP and/or Fas antibody may be used in conjunction with an anti-cancer agent, chemotherapy, radiotherapy, etc. (e.g., simultaneously, or as part of an overall treatment procedure). The term "cancer treatment" as used herein, may include, but is not limited to, chemotherapy, radiotherapy, adjuvant therapy, vaccination, or any combination of these methods. Aspects of cancer treatment that may vary include, but are not limited to, dosages, timing of administration or duration or therapy; and the cancer treatment can vary in dosage, timing, or duration. Another treatment for cancer is surgery, which can be utilized either alone or in combination with any of the previously treatment methods. One of ordinary skill in the medical arts can determine an appropriate treatment for a subject.

In one embodiment, the cancer treatment may include treatment with an anti-cancer agent or drug, for example, a conventionally-known anti-cancer agent or drug. Examples of suitable anti-cancer agents and drugs include, but are not limited to, 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B. betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, carn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflomithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalFasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, and zorubicin hydrochloride, as well as salts, homologs, analogs, derivatives, enantiomers and/or functionally equivalent compositions thereof.

In one set of embodiments, cells may be removed from a tumor (e.g., a tumor from a subject, a tumor growing in vitro, etc.) and exposed in some Fashion to the systems and methods described herein. For example, the cells may be manipulated to increase the amount of UCP in the plasma membrane (e.g., by exposure to a fatty acid metabolic inhibitor) and/or manipulated to inhibit UCP function (e.g., by exposure to a UCP inhibitor).

After suitable exposure, the exposed cells may be introduced into a subject. In one embodiment, exposure of the cells may alter the immunological profile of the tumor cells in some Fashion, for example, such that a subject's immune system is able to recognize the tumor cells. The subject's immune system, after interacting with the exposed cells, may then be able to recognize tumors present within the subject, thus causing the cancer to decrease. If the subject has a tumor, the cells may be injected into the tumor, proximate the tumor, and/or systemically or locally delivered in a region of the body away from the tumor. In some cases, a tumor may be removed from a subject, then the exposed cells may be inserted, e.g., into the cavity created upon removal of the tumor, or to another site within the body. Optionally, other cancer treatment methods, such as radiation or exposure to conventional anti-cancer agents, may also be used in conjunction with these methods. In some cases, the subject may not have a cancer or tumor, but the cells may be injected to stimulate the immune system to produce antibodies against future cancers and/or other uncontrolled cellular growths, i.e., "immunizing" the subject from cancer and/or other uncontrolled cellular growths.

In some the cancer cells are antigenic and can be targeted by the immune system. Thus, the combined administration of the systems and methods of the invention and cancer medicaments, particularly those which are classified as cancer immunotherapies, can be very useful for stimulating a specific immune response against a cancer antigen. A "cancer antigen" as used herein is a compound, such as a peptide, associated with a tumor or cancer cell surface, and which is capable of provoking an immune response when expressed on the surface of an antigen-presenting cell in the context of an MHC molecule. Cancer antigens, such as those present in cancer vaccines or those used to prepare cancer immunotherapies, can be prepared from crude cancer cell extracts, e.g., as described in Cohen, et al., *Cancer Research*, 54:1055, 1994, or by partially purifying the antigens, using recombinant technology, or de novo synthesis of known antigens. Cancer antigens can be used in the form of immunogenic portions of a particular antigen, or in some instances, a whole cell or a tumor mass can be used as the antigen. Such antigens can be isolated or prepared recombinantly or by any other means known in the art.

The systems and methods of the invention can be used in combination with immunotherapeutics in certain cases. The goal of immunotherapy is to augment a subject's immune response to an established tumor. One method of immunotherapy includes the use of adjuvants. Adjuvant substances derived from microorganisms, such as bacillus Calmette-Guerin, can heighten the immune response and enhance resistance to tumors in animals. Immunotherapeutic agents are often medicaments that derive from antibodies or antibody fragments that specifically bind to or otherwise recognize a cancer antigen. Binding of such agents can promote an immune response, such as an antigen-specific immune response. Antibody-based immunotherapies may function by binding to the cell surface of a cancer cell, which can stimulate the endogenous immune system to attack the cancer cell.

As used herein, a "cancer antigen" is broadly defined as an antigen expressed by a cancer cell. The antigen can be expressed at the cell surface of the cancer cell. In many cases, the antigen is one that is not expressed by normal cells, or at least not expressed at the same level or concentration as in cancer cells. As examples, some cancer antigens are normally silent (i.e., not expressed) in normal cells, some are expressed only at certain stages of differentiation, and others are only temporally expressed (such as embryonic and fetal antigens). Other cancer antigens are encoded by mutant cellular genes, such as oncogenes (e.g., activated ras oncogene), suppressor genes (e.g., mutant p53), fusion proteins resulting from internal deletions or chromosomal translocations, or the like. Still other cancer antigens can be encoded by viral genes, such as those carried on RNA and DNA tumor viruses. The differential expression of cancer antigens in normal and cancer cells can be exploited in order to target cancer cells in some cases. As used herein, the terms "cancer antigen" and "tumor antigen" are used interchangeably.

The theory of immune surveillance is that a prime function of the immune system is to detect and eliminate neoplastic cells before a tumor forms. A basic principle of this theory is that cancer cells are antigenically different from normal cells and thus can elicit immune reactions similar to those that cause rejection of immunologically incompatible allografts. Studies have confirmed that tumor cells differ, qualitatively or quantitatively, in their expression of antigens. For example, "tumor-specific antigens" are antigens that are specifically associated with tumor cells but not normal cells. Examples of tumor specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

Different types of cells that can kill tumor targets in vitro and in vivo have been identified: natural killer cells (NK cells), cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK and CTL populations. Activated macrophages can kill tumor cells in a manner that is not antigen-dependent, nor MHC-restricted, once activated. Activated macrophages are thought to decrease the growth rate of the tumors they infiltrate. In vitro assays have identified other immune mechanisms such as antibody-dependent, cell-mediated cytotoxic reactions, and lysis by antibody plus complement. However, these immune effector mechanisms are thought to be less important in vivo than the function of NK, CTLs, LAK, and macrophages in vivo (for a review, see Piessens, "Tumor Immunology," in *Scientific American Medicine*, Vol. 2, Scientific American Books, p. 1-13, 1996).

In one embodiment, the immunotherapeutic agent may function as a delivery system for the specific targeting of toxic substances to cancer cells. For example, the agent may be conjugated to toxins such as ricin (e.g., from castor beans), calicheamicin, maytansinoids, radioactive isotopes such as iodine-131 and yttrium-90, chemotherapeutic agents, and/or to biological response modifiers. In this way, the toxic substances can be concentrated in the region of the cancer and non-specific toxicity to normal cells can be minimized.

In another embodiment, the immunotherapeutic agent may be directed towards the binding of vasculature, such as those that bind to endothelial cells. This is because solid tumors are generally dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

In another set of embodiments, the combined administration of the systems and methods of the invention and an apoptotic chemotherapeutic agent may be used. An "apoptotic chemotherapeutic agent," as used herein, includes molecules that function by a variety of mechanisms to induce apoptosis in rapidly dividing cells. Apoptotic chemotherapeutic agents are a class of chemotherapeutic agents that are well known to those of ordinary skill in the art. Chemotherapeutic agents include those agents disclosed in Chapter 52, "Antineoplastic Agents" (Paul Calabresi and Bruce A. Chabner), and the introduction thereto, p. 1202-1263, of Goodman and Gilman's *The Pharmacological Basis of Therapeutics*, Eighth Edition, McGraw-Hill, Inc. Health Professions Division, 1990, incorporated herein by reference. Suitable chemotherapeutic agents may have various mechanisms of action. Classes of suitable chemotherapeutic agents include, but are not limited to: (a) alkylating agents, such as nitrogen mustard (e.g. mechlorethamine, cylophosphamide, ifosfamide, melphalan, chlorambucil), ethylenimines and methylmelamines (e.g. hexamethylmelamine, thiotepa), alkyl sulfonates (e.g. busulfan), nitrosoureas (e.g. carmustine, which is also known as BCNU, lomustine which is also known as CCNU, semustine, which is also known as methyl-CCNU, chlorozoticin, streptozocin), and triazines (e.g. dicarbazine, which is also known as DTIC); (b) antimetabolites, such as folic acid analogs (e.g. methotrexate), pyrimidine analogs (e.g. 5-fluorouracil floxuridine, cytarabine, and azauridine and its prodrug form azaribine), and purine analogs and related materials (e.g. 6-mercaptopurine, 6-thioguanine, pentostatin); (c) natural products, such as the vinca alkaloids (e.g. vinblastine, vincristine), epipodophylotoxins (e.g. etoposide, teniposide), antibiotics (e.g. dactinomycin, which is also known as actinomycin-D, daunorubicin, doxorubicin, bleomycin, plicamycin, mitomycin, epirubicin, which is 4-epidoxorubicin, idarubicin which is 4-dimethoxydaunorubicin, and mitoxanthrone), enzymes (e.g. L-asparaginase), and biological response modifiers (e.g. interferon alfa); (d) miscellaneous agents, such as the platinum coordination complexes (e.g. cisplatin, carboplatin), substituted ureas (e.g. hydroxyurea), methylhydiazine derivatives (e.g. procarbazine), adreocortical suppressants (e.g. mitotane, aminoglutethimide) taxol; (e) hormones and antagonists, such as adrenocorticosteroids (e.g. prednisone or the like), progestins (e.g. hydroxyprogesterone caproate, medroxyprogesterone acetate, megestrol acetate), estrogens (e.g. diethyestilbestrol, ethinyl estradiol, or the like), antiestrogens (e.g. tamoxifen), androgens (e.g. testosterone propionate, fluoxymesterone, or the like), antiandrogens (e.g. flutamide), and gonadotropin-releasing hormone analogs (e.g. leuprolide), and (f) DNA damaging compounds, such as adriamycin. The combined administration of the systems and methods of the invention and an apoptotic chemotherapeutic agent effective to inhibit growth of the tumor cell is that amount effective to induce apoptosis of the tumor cell in some cases.

In yet another set of embodiments, the systems and methods of the invention may be used in conjunction with a cancer vaccine. Cancer vaccines are medicaments that are intended to stimulate an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes that are capable of killing tumor cells. Cancer vaccines generally enhance the presentation of cancer antigens to both antigen-presenting cells (e.g., macrophages and dendritic cells) and/or to other immune cells such as T cells, B cells, and NK cells.

Although cancer vaccines may take one of several forms, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine, which is a preparation of cancer cells that have been removed from a subject, treated ex vivo and then reintroduced as whole cells in the subject. Lysates of tumor cells can also be used as cancer vaccines to elicit an immune response in certain cases. Another form of cancer vaccine is a peptide vaccine, which uses cancer-specific or cancer-associated small proteins to activate T cells. Cancer-associated proteins are proteins that are not exclusively expressed by cancer cells (i.e., other normal cells may still express these antigens). However, the expression of cancer-associated antigens is generally consistently upregulated with cancers of a particular type. Yet another form of cancer vaccine is a dendritic cell vaccine, which includes whole dendritic cells that have been exposed to a cancer antigen or a cancer-associated antigen in vitro. Lysates or membrane fractions of dendritic cells may also be used as cancer vaccines in some instances. Dendritic cell vaccines are able to activate antigen-presenting cells directly. Other non-limiting examples of cancer vaccines include ganglioside vaccines, heat-shock protein vaccines, viral and bacterial vaccines, and nucleic acid vaccines.

In come embodiments, cancer vaccines may be used along with adjuvants. Adjuvants are substances that activate the subject's immune system, and can be used as an adjunct therapy in any of the systems or methods of the invention. Adjuvants include, for example, alum, QS STIMULON® (Aquila), MF-59 (CHIRON®), DETOX™ (RIBI IMMUNOCHEM RESEARCH INC.®), OPTIVAX® (VAXCELS™) and LeIF (CORIXA®).

Other cancer vaccines take the form of dendritic cells that have been exposed to cancer antigens in vitro, have processed the antigens and are able to express the cancer antigens at their cell surface in the context of MHC molecules for effective antigen presentation to other immune system cells.

The invention, in still another aspect, is useful for treating other diseases associated with rapidly dividing cells, such as rheumatoid arthritis and scleroderma. Rheumatoid arthritis is associated in its early stages with the rapid division of synoviocytes. This process is referred to a pannus formation. The rapidly dividing cells produce a substance that kills osteocytes leading to the hardening of the tissue.

In another aspect, the systems and methods of the invention are useful in treating wounds in subjects. As used herein, the term "wound" is used to describe skin wounds as well as tissue wounds. A "skin wound" is defined herein as a break in the continuity of skin tissue that is caused by direct injury to the skin. Skin wounds are generally characterized by several classes including punctures, incisions, including those produced by surgical procedures, excisions, lacerations, abrasions, atrophic skin, or necrotic wounds and burns. The systems and methods of the invention are useful for enhancing the healing of all wounds of the skin.

A "tissue wound," as used herein, is a wound to an internal organ, such as a blood vessel, intestine, colon, etc. The systems and methods of the invention are useful for enhancing the wound healing process in tissue wounds, whether they arise naturally, or as the result of surgery. For instance, during the repair of arteries an artery may need to be sealed and wound healing promoted as quickly as possible. The systems and methods of the invention can speed up that process in many cases. The invention may also be particularly useful for the treatment of damaged tissue in the colon. In addition to promoting wound healing of the damaged colon, in some cases, the systems and methods of the invention can provide an antimicrobial effect.

The cells treated according to the present invention may be used to treat a wound. For example, ex vivo cells may be attached to a bandage or other substrate, and the substrate positioned over a wound, at least partially covering the wound. In some cases, the bandage or other substrate may be adhered to the subject, for example, through the use of adhesives. Suitable adhesives can be selected by those of ordinary skill in the art; some suitable adhesives are further described below.

The systems and methods of the invention may also include additional therapeutic and/or pharmacologically acceptable agents. For instance, the compositions or methods may involve other agents for the treatment of wounds such as, for instance, dexpanthenol, growth factors, enzymes or hormones, povidon-iodide, fatty acids, such as cetylphridinium chloride, antibiotics, and analgesics. In some embodiments, the compositions may also include growth factors. Growth factors include, but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-alpha, TGF-beta, cartilage inducing factors-A and -B, osteoid-inducing factors, osteogenin and other bone growth factors, collagen growth factors, heparin-binding growth factor-1 or -2, and/or their biologically active derivatives. The compositions may also include antiseptics in some embodiments.

In another aspect, the systems and methods of the invention are useful for treating or preventing disorders associated with a specific antigenic immune response. Thus, in some embodiments of the invention, the methods are used to treat mammals at risk of, or afflicted with, autoimmune disease. Autoimmune disease is a disorder in which the host's immune response is defective and results in the production of a specific immune response against the individual's own antigens or components. In an autoimmune disease, an individual's own antibodies react with host tissue or in which immune effector T cells are autoreactive to endogenous self-peptides and cause destruction of tissue. It is well established that MHC class II alleles act as major genetic elements in susceptibility to a variety of autoimmune diseases. The structures recognized by T cells, the cells that cause autoimmunity, are complexes comprised of class II MHC molecules and antigenic peptides. When the T cells react with the host's class II MHC molecules-peptide complexes derived from a host's own gene products, autoimmune disease can result. If these class II MHC/peptide complexes are inhibited from being formed, the autoimmune response is reduced or suppressed, and thus is inhibited according to the invention. The peptide-antigen of autoimmune disorders are self-antigens. Any autoimmune disease in which class II MHC/peptide complexes play a role may be treated according to the methods of the present invention. Such autoimmune diseases include, but are not limited to, juvenile-onset diabetes (insulin-dependent), multiple sclerosis, pemphigus vulgaris, Graves's disease, myasthenia gravis, systemic lupus erythematosus (SLE), celiac disease rheumatoid arthritis, and Hashimoto's thyroiditis. The invention includes a method for determining an individual's susceptibility to developing autoimmune disease. As used herein, "susceptibility to autoimmune disease" indicates a likelihood of at least greater than the average of developing autoimmune disease, and in some embodiments at least about 10% greater. Thus the invention also includes systems and methods for treating a subject having autoimmune disease to reduce associated cell death.

When used with mammalian cells in vitro, certain systems and methods may have utility for loading of specific antigens within the MHC molecules. Cells with specific antigen loading in class II molecules have utility in a variety of analytical and diagnostic assays. These cells are also useful as therapeutic agents. For instance, the cells can be used in culture to study immune responses or to screen the effect of putative drugs on inhibiting or promoting antigen-specific immune responses. Additionally, the cells could be administered to a mammalian subject to promote an antigen-specific T cell response. When administered to a subject, the class II MHC/ antigen complexes on the surface of the cell can interact with endogenous T cells, inducing an immune cascade, and thus can produce an antigen-specific immune response. In some embodiments, the cells manipulated in vitro have been isolated from the same subject ex vivo.

The systems and methods of the invention can also be used for treating a mammalian subject in vivo to induce an antigen-specific immune response. It is useful to produce antigen-specific immune responses against any foreign antigen, whether it is capable of causing a pathological state and/or any damage to its mammalian host. The terms "foreign antigen" or "antigen" are used synonymously to refer to a molecule capable of provoking an immune response in a host, wherein the antigen is not a self-antigen, as defined above. Thus, these terms specifically excludes self-antigens. Self-antigens are used herein to refer to the peptide-antigens of autoimmune disorders. An immune response against the self-antigen results in an autoimmune disorder. The term "self-antigen" does not include, however, antigens such as cancer antigens, which are recognized by the host as foreign and which are not associated with autoimmune disease. Thus, the term "antigen" specifically excludes self-antigens and broadly includes any type of molecule (e.g. associated with a host or foreign cell) that is recognized by a host immune system as being foreign. Antigens include, but are not limited to, cancer antigens and microbial antigens and may be composed of cells, cell extracts, polysaccharides, polysaccharide conjugates, lipids, glycolipids, carbohydrates, peptides, proteins, viruses, viral extracts, etc. A "cancer antigen," as used herein, is a compound which is associated with a tumor or cancer cell surface and which is capable of provoking an immune response when expressed on the surface of an antigen-presenting cell in the context of a class II MHC molecule. Cancers or tumors include those described above.

Cancer antigens include but are not limited to Melan-A/MART-1, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, alpha-fetoprotein, E-cadherin, alpha-catenin, beta-catenin and gamma-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1 and CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, Imp-1, EBV-encoded nuclear antigen (EBNA)-1, or c-erbB-2.

In some embodiments, cancers or tumors escaping immune recognition and tumor-antigens associated with such tumors (but not exclusively), include acute lymphoblastic leukemia (etv6; aml1; cyclophilin b), B cell lymphoma (Ig-idiotype), glioma (E-cadherin; alpha-catenin; beta-catenin; gamma-catenin; p120ctn), bladder cancer (p21ras), billiary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)-C017-1A/GA733; APC), choriocarcinoma (CEA), epithelial cell-cancer (cyclophilin b), gastric cancer (HER2/neu; c-erbB-2; ga733 glycoprotein), hepatocellular cancer (alpha-fetoprotein), hodgkins lymphoma (Imp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21ras), non-small cell lung carcinoma (HER2/neu; c-erbB-2), nasopharyngeal cancer (Imp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal (HER2/neu; c-erbB-2), squamous cell cancers of cervix and esophagus (viral products such as human papilloma virus proteins), testicular cancer (NY-ESO-1), T cell leukemia (HTLV-1 epitopes), and melanoma (Melan-A/MART-1; cdc27; MAGE-3; p21ras; gp100$^{Pmel117}$).

For examples of tumor antigens which bind to either or both MHC class I and MHC class II molecules, see the following references: Coulie, *Stem Cells,* 13:393-403, 1995; Traversari, et al., *J. Exp. Med.,* 176:1453-1457, 1992; Chaux, et al., *J. Immunol.,* 163:2928-2936, 1999; Fujie, et al., *Int. J. Cancer,* 80:169-172, 1999; Tanzarella, et al., *Cancer Res.,* 59:2668-2674, 1999; van der Bruggen, et al., *Eur. J. Immunol.,* 24:2134-2140, 1994; Chaux, et al., *J. Exp. Med.,* 189:767-778, 1999; Kawashima et al, *Hum. Immunol.,* 59:1-14, 1998; Tahara, et al., *Clin. Cancer Res.,* 5:2236-2241, 1999; Gaugler, et al., *J. Exp. Med.,* 179:921-930, 1994; van der Bruggen, et al., *Eur. J. Immunol.,* 24:3038-3043, 1994; Tanaka, et al., *Cancer Res.,* 57:4465-4468, 1997; Oiso, et al., *Int. J. Cancer,* 81:387-394, 1999; Herman, et al., *Immunogenetics,* 43:377-383, 1996; Manici, et al., *J. Exp. Med.,* 189:871-876, 1999; Duffour, et al., *Eur. J. Immunol.,* 29:3329-3337, 1999; Zorn, et al., *Eur. J. Immunol.,* 29:602-607, 1999; Huang, et al., *J. Immunol.,* 162:6849-6854, 1999; Boël, et al., *Immunity,* 2:167-175, 1995; Van den Eynde, et al., *J. Exp. Med.,* 182:689-698, 1995; De Backer, et al., *Cancer Res.,* 59:3157-3165, 1999; Jäger, et al., *J. Exp. Med.,* 187:265-270, 1998; Wang, et al., *J. Immunol.,* 161:3596-3606, 1998; Aarnoudse, et al., *Int. J. Cancer,* 82:442-448, 1999; Guilloux, et al., *J. Exp. Med.,* 183:1173-1183, 1996; Lupetti, et al., *J. Exp. Med.,* 188:1005-1016, 1998; Wölfel, et al., *Eur. J. Immunol.,* 24:759-764, 1994; Skipper, et al., *J. Exp. Med.,* 183:527-534, 1996; Kang, et al., *J. Immunol.,* 155:1343-1348, 1995; Morel, et al., *Int. J. Cancer,* 83:755-759, 1999; Brichard, et al., *Eur. J. Immunol.,* 26:224-230, 1996; Kittlesen, et al., *J. Immunol.,* 160:2099-2106, 1998; Kawakami, et al., *J. Immunol.,* 161:6985-6992, 1998; Topalian, et al., *J. Exp. Med.,* 183:1965-1971, 1996; Kobayashi, et al., *Cancer Res.,* 58:296-301, 1998; Kawakami, et al., *J. Immunol.,* 154:3961-3968, 1995; Tsai, et al., *J. Immunol.,* 158:1796-1802, 1997; Cox, et al., *Science,* 264:716-719, 1994; Kawakami, et al., *Proc. Natl. Acad. Sci. U.S.A.,* 91:6458-6462, 1994; Skipper, et al., *J. Immunol.,* 157:5027-5033, 1996; Robbins, et al., *J. Immunol.,* 159:303-308, 1997; Castelli et al, *J. Immunol.,* 162:1739-1748, 1999; Kawakami, et al., *J. Exp. Med.,* 180:347-352, 1994; Castelli, et al., *J. Exp. Med.,* 181:363-368, 1995; Schneider, et al., *Int. J. Cancer,* 75:451-458, 1998; Wang, et al., *J. Exp. Med.,* 183:1131-1140, 1996; Wang, et al., *J. Exp. Med.,* 184:2207-2216, 1996; Parkhurst, et al., *Cancer Res.,*

58:4895-4901, 1998; Tsang, et al., *J. Natl. Cancer Inst.*, 87:982-990, 1995; Correale, et al., *J. Natl. Cancer Inst.*, 89:293-300, 1997; Coulie, et al., *Proc. Natl. Acad. Sci. U.S.A.*, 92:7976-7980, 1995; Wölfel, et al., *Science*, 269: 1281-1284, 1995; Robbins, et al., *J. Exp. Med.*, 183:1185-1192, 1996; Brändle, et al., *J. Exp. Med.*, 183:2501-2508, 1996; ten Bosch, et al., *Blood*, 88:3522-3527, 1996; Mandruzzato, et al., *J. Exp. Med.*, 186:785-793, 1997; Guéguen, et al., *J. Immunol.*, 160:6188-6194, 1998; Gjertsen, et al., *Int. J. Cancer*, 72:784-790, 1997; Gaudin, et al., *J. Immunol.*, 162: 1730-1738, 1999; Chiari, et al., *Cancer Res.*, 59:5785-5792, 1999; Hogan, et al., *Cancer Res.*, 58:5144-5150, 1998; Pieper, et al., *J. Exp. Med.*, 189:757-765, 1999; Wang, et al., *Science*, 284:1351-1354, 1999; Fisk, et al., J. Exp. Med. 181:2109-2117, 1995; Brossart, et al., *Cancer Res.*, 58:732-736, 1998; Röpke, et al., *Proc. Natl. Acad. Sci. U.S.A.*, 93:14704-14707, 1996; Ikeda, et al., *Immunity* 6:199-208, 1997; Ronsin, et al., *J. Immunol.*, 163:483-490, 1999; or Vonderheide, et al., *Immunity*, 10:673-679, 1999. These antigens as well as others are disclosed in PCT Application PCT/US98/18601.

The systems and methods of the invention are also useful for treating mammals at risk of, or afflicted with, allergic responses. An "allergic response" as used herein is a disorder in which the host's immune response to a particular antigen is unnecessary or disproportionate, resulting in pathology. An allergic response may occur, in part, because a T cell recognizes a particular class II MHC/peptide complex and triggers a cascade of immune response. If the class II MHC/peptide complex is inhibited from being formed, the allergic response is reduced or suppressed. Any allergic response in which class II MHC/peptide complexes play a role may be treated according to the methods of the present invention. Allergies arising from an allergic response include, but are not limited to, allergies to pollen, ragweed, shellfish, domestic animals, (e.g., cats and dogs), B-venom, and the like. A subset of allergic responses produce asthma. Allergic asthmatic responses are also included within the definition of the term "allergic response." It is particularly desirable to treat severe or life-threatening allergic responses, such as those arising during asthmatic attacks or anaphylactic shock, according to the systems and methods of the invention.

In another aspect, the systems and methods of the invention are also useful for treating mammals that have undergone or about to undergo, an organ transplant or tissue graft. In tissue transplantation (e.g., kidney, lung, liver, heart) or skin grafting, when there is a mismatch between the class II MHC genotypes (HLA types) of the donor and recipient, there may be a severe "allogeneic immune response" against the donor tissues which results from the presence of non-self or allogeneic class II MHC molecules presenting antigenic peptides on the surface of donor cells.

The systems and methods of the invention, in yet another aspect, are useful for treating mammals having an inflammatory disease or condition. An "inflammatory disease or condition," as used herein, refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil activation. These conditions include, but are not limited to, meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

In one aspect, the compositions of the invention can also be used in combination with other therapies, such as radiation therapy. When a combination of therapies are used the effective amount to achieve the desired result, inhibition of cell proliferation may be less. This may reduce or eliminate any side effects associated with high concentrations of the individual therapies. One example is a combination of one or more compositions of the invention and radiation therapy. In some cases, the radiation therapy may also contribute to the inhibition of UCP in the plasma membrane. Radiation-sensitive cells are those cells that express UCP in the plasma membrane, and radioresistant cells do not express plasma membrane UCP. The invention also includes, in some instances, systems and methods of treating radioresistant cells by inducing UCP expression in the plasma membrane and treating them with radiation.

Optionally, in some embodiments, a targeting mechanism can be used to target one or more compositions of the invention to a specific cell, tumor, wound, or the like. It is desirable in many instances to specifically target a cell type to increase the efficiency and specificity of administration of the composition, thus avoiding the effects that can damage or destroy unrelated cells. Thus, a delivery system that enables the delivery of such drugs specifically to target cells is provided. The delivery system may increase the efficacy of treatment and reduce the associated "side effects" of such treatment.

Methods of targeting drugs and other compositions to target cells (such as cancer cells or cells within a wound) are well known in the art. One method of targeting involves antibody or receptor targeting. Receptor or antibody targeting involves linking the compound of the invention to a ligand or an antibody that has an affinity for a receptor or cell surface molecule expressed on the desired target cell surface, for example, UCP. Using this approach, a composition of the invention is intended to adhere to the target cell following formation of a ligand-receptor or antibody-cell surface antigen complex on the cell surface. The type of receptor or antibody used to target the cell will depend on the specific cell type being targeted. A target molecule may be attached by a peptide or other type of bond such as a sulfhydryl or disulfide bond. Targeting molecules are described, for instance in U.S. Pat. No. 5,849,718, as well as many other references.

In general, the targeting moiety can be coupled to a composition of the invention. The molecules may be directly coupled to one another, such as by conjugation, or may be indirectly coupled to one another where, for example, the targeting moiety is on the surface of a liposome and one or more compositions of the invention are contained within the liposome. If the molecules are linked to one another, then the targeting moiety can be covalently or noncovalently bound to the compound of the invention in a manner that preserves the targeting specificity of the targeting moiety. As used herein, "linked" or "linkage" means two entities are bound to one another by any physiochemical means. It is important that the linkage be of such a nature that it does not impair substantially the effectiveness of the compositions of the invention or the binding specificity of the targeting moiety. Keeping these parameters in mind, any linkage known to those of ordinary skill in the art may be employed, covalent or noncovalent. Such means and methods of linkage are well known to those of ordinary skill in the art.

Linkages according to the invention need not be direct linkage. The compositions of the invention may be provided with functionalized groups to facilitate their linkage and/or linker groups may be interposed therebetween to facilitate their linkage. In some instances, the components of the present invention may be synthesized in a single process, whereby the composition is regarded as a single entity. For example, a targeting moiety specific for a tumor cell could be synthesized together with a VCP inhibitor and a fatty acid metabolism inhibitor of the invention. These and other modifications are intended to be embraced by the present invention.

Specific examples of covalent bonds include those where bifunctional cross-linker molecules can be used. The cross-linker molecules may be homobifunctional or heterobifunctional, depending upon the nature of the molecules to be conjugated. Homobifunctional cross-linkers have two identical reactive groups. Heterobifunctional cross-linkers have two different reactive groups that allow sequential conjugation reaction. Various types of commercially available cross-linkers are reactive with one or more of the following groups, such as primary amines, secondary amines, sulfhydriles, carboxyls, carbonyls and carbohydrates.

Non-covalent methods of conjugation also may be used to join the targeting moiety and the composition in some cases. Non-covalent conjugation may be accomplished by direct or indirect means, including hydrophobic interaction, ionic interaction, intercalation, binding to major or minor grooves of a nucleic acid, and other affinity interactions.

Covalent linkages may be noncleavable in physiological environments, or cleavable in physiological environments, such as linkers containing disulfide bonds. Such molecules may resist degradation and/or may be subject to different intracellular transport mechanisms. One of ordinary skill in the art will be able to ascertain, without undue experimentation, the preferred bond for linking the targeting moiety and the compositions of the invention, based on the chemical properties of the molecules being linked and the preferred characteristics of the bond, for a given application.

For indirect linkage, the targeting moiety may be part of a particle, such as a liposome, which is targeted to a specific cell type. The liposome, in turn, may contain the compositions of the invention. The manufacture of liposomes containing compositions of the invention is fully described in the literature. Many for example, are based upon cholesteric molecules as starting ingredients and/or phospholipids. They may be synthetically derived or isolated from natural membrane components. Virtually any hydrophobic substance can be used, including cholesteric molecules, phospholipids and fatty acids preferably of medium chain length (i.e., 12 to 20 carbons), for example, naturally occurring fatty acids of between 14 and 18 carbons in length. These molecules can be attached to one or more compositions of the invention, for example, with the lipophilic anchor inserting into the membrane of a liposome and the compositions tethered on the surface of the liposome for targeting the liposome to the cell. In other cases, one or more compositions of the invention may be present in the interior of the liposome.

Each of the compositions of the invention (or portions thereof) may optionally be associated with a delivery system or vector, in one aspect. In its broadest sense, a "vector" is any vehicle capable of facilitating: (1) delivery of a composition to a target cell or (2) uptake of a composition by a target cell, if uptake is important. Optionally, a "targeting ligand" (in addition to, or the same as, the plasma membrane targeting molecule) can be attached to the vector to selectively deliver the vector to a cell that expresses on its surface the cognate receptor for the targeting ligand. In this manner, the vector (containing one or more compositions of the invention) can be selectively delivered to a cell in, e.g., a tumor, a wound, etc. In general, the vectors useful in the invention are divided into two classes: colloidal dispersion systems and biological vectors. Other example compositions that can be used to facilitate uptake by a target cell of compositions of the invention include calcium phosphate and other chemical mediators of intracellular transport, microinjection compositions, and electroporation.

In general, the vectors useful in the invention include, but are not limited to, plasmids, phagemids, viruses, other vehicles derived from viral or bacterial sources that have been manipulated by the insertion or incorporation of the UCP and/or Fas inhibitor nucleic acid sequences. Viral vectors include, but are not limited to, nucleic acid sequences from any of the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named above but known to the art.

In some cases, the viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in the literature, e.g., Kriegler, *Gene Transfer and Expression, A Laboratory Manual*, W.H. Freeman, Co., 1990 and Murry, Ed. *Methods in Molecular Biology*, Vol. 7, Humana Press, Inc., 1991.

A virus useful for certain applications is an adeno-associated virus, which is a double-stranded DNA virus. The adeno-associated virus can be engineered to be replication-deficient and is capable of infecting a wide range of cell types and species in many cases. It further has certain advantages, such as heat and lipid solvent stability; high transduction frequencies in cells of diverse lineages, including hemopoietic cells; and lack of superinfection inhibition, thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extra chromosomal Fashion.

Other suitable vectors include plasmid vectors. Plasmid vectors have been extensively described in the art and are well known to those of skill in the art. See e.g., Sambrook, et al., *Molecular Cloning: A Laboratory Manual*, Second Edition, Cold Spring Harbor Laboratory Press, 1989. Plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and/or ligation reactions to remove and add specific fragments of DNA.

It has also been discovered that gene-carrying plasmids can be delivered to the cells in vivo using bacteria. Modified forms of bacteria such as Salmonella can be transfected with the plasmid and can thus be used as delivery vehicles in some cases. The bacterial delivery vehicles can be administered to a host subject orally or by other administration means. The bacteria in some instances can pass through the gut barrier. High levels of expression have been established using this methodology.

Compaction agents also can be used alone, or in combination with, a vector of the invention. A "compaction agent," as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the compositions in a form that is more efficiently taken up by the cell or, more preferably, in combination with one or more of the above-described vectors.

In one aspect, the invention provides a method of administering any of the compositions described herein to a subject. When administered, the compositions are applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the subject. Any of the compositions of the present invention may be administered to the subject in a therapeutically effective dose. The dose to the subject may be such that a therapeutically effective amount of one or more active compounds reaches the active site(s) within the subject. A "therapeutically effective" or an "effective" dose, as used herein, means that amount necessary to delay the onset of, inhibit the progression of, halt altogether the onset or progression of, diagnose a particular condition being treated, or otherwise achieve a medically desirable result, i.e., that amount which is capable of at least partially preventing, reversing, reducing, decreasing, ameliorating, or otherwise suppressing the particular condition being treated. A therapeutically effective amount can be determined on an individual basis and will be based, at least in part, on consideration of the species of mammal, the mammal's age, sex, size, and health; the composition used, the type of delivery system used; the time of administration relative to the severity of the disease; and whether a single, multiple, or controlled-release dose regiment is employed. A therapeutically effective amount can be determined by one of ordinary skill in the art employing such factors and using no more than routine experimentation.

The terms "treat," "treated," "treating," and the like, when used herein, refer to administration of the systems and methods of the invention to a subject, which may, for example, increase the resistance of the subject to development or further development of cancers, to eliminate or at least control a cancer or a wound, and/or to reduce the severity of the cancer or wound. The pharmaceutical preparations of the invention are administered to subjects in effective amounts. When administered to a subject, effective amounts will depend on the particular condition being treated and the desired outcome. A therapeutically effective dose may be determined by those of ordinary skill in the art, for instance, employing factors such as those further described below and using no more than routine experimentation.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day. As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parental administration, in some cases, may be from one to several orders of magnitude lower dose per day, as compared to oral doses. For example, the dosage of an active compound, when parentally administered, may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day.

In some embodiments, the concentration of the active compound(s) of the composition, if administered systemically, is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. If applied topically, the concentration may be about 0.1 mg to about 500 mg/g of ointment or other base, about 1.0 mg to about 100 mg/g of base, or about 30 mg to about 70 mg/g of base. The specific concentration partially depends upon the particular composition used, as some are more effective than others. The dosage concentration of the composition actually administered is dependent, at least in part, upon the particular disorder being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously effect the mammal.

The dosage may be given in some cases at the maximum amount while avoiding or minimizing any potentially detrimental side effects within the subject. The dosage actually administered can be dependent upon factors such as the final concentration desired at the active site, the method of administration to the subject, the efficacy of the composition, the longevity of the composition within the subject, the mode and/or timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, active site of the cancer or wound, or current state of health of the subject may also influence the dose required and/or the concentration of the composition at the active site. Variations in dosing may occur between different individuals or even within the same individual on different days. These factors are well known to those of ordinary skill in the art and can be addressed with no more than routine experimentation. It is preferred that a maximum dose be used, that is, the highest safe dose according to sound medical judgment.

In the event that the response of a particular subject is insufficient at such doses, even higher doses (or effectively higher doses by a different, more localized delivery route)

may be employed to the extent that subject tolerance permits. Multiple doses per day are also contemplated, in some cases, to achieve appropriate systemic levels within the subject or within the active site of the subject. In certain instances, dosing amounts, dosing schedules, routes of administration, and the like may be selected as described herein, whereby therapeutically effective levels of the composition are provided.

In certain embodiments where cancers are being treated, a composition of the invention is administered to a subject who has a family history of cancer, or to a subject who has a genetic predisposition for cancer. In other embodiments, the composition is administered to a subject who has reached a particular age, or to a subject more likely to get cancer. In yet other embodiments, the compositions is administered to subjects who exhibit symptoms of cancer (e.g., early or advanced). In still other embodiments, the composition may be administered to a subject as a preventive measure. In some embodiments, the inventive composition may be administered to a subject based on demographics or epidemiological studies, or to a subject in a particular field or career.

Administration of a composition of the invention to a subject may be accomplished by any medically acceptable method that allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active compound(s) of the composition within the subject without causing clinically unacceptable adverse effects. The administration may be localized (i.e., to a particular region, physiological system, tissue, organ, or cell type) or systemic, depending on the condition being treated. For example, the composition may be administered orally, vaginally, rectally, buccally, pulmonary, topically, nasally, transdermally, through parenteral injection or implantation, via surgical administration, or any other method of administration where suitable access to a target is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the composition. Other oral compositions suitable for use with the invention include solutions or suspensions in aqueous or non-aqueous liquids such as a syrup, an elixir, or an emulsion. In one set of embodiments, the composition may be used to fortify a food or a beverage.

Injections can be e.g., intravenous, intradermal, subcutaneous, intramuscular, or interperitoneal. For example, the inhibitor can be injected intravenously or intramuscularly for the treatment of multiple sclerosis, or can be injected directly into the joints for treatment of arthritic disease, or can be injected directly into the lesions for treatment of pemphigus vulgaris. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. For systemic administration, it may be useful to encapsulate the composition in liposomes.

Inhalation includes administering the composition with an aerosol in an inhaler, either alone or attached to a carrier that can be absorbed.

In general, the compositions of the invention may be delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those of ordinary skill in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth) acrylic acid, polyamides, copolymers and mixtures thereof.

Bioadhesive polymers of particular interest in some cases include, but are not limited to, the bioerodible hydrogels described by Sawhney, et al., *Macromolecules*, 26:581-587, 1993, the teachings of which are incorporated herein, as well as polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The systems and methods of the invention can be administered by any method that allows the composition of the invention to reach the target cells, e.g., tumor cells. These methods include, e.g., injection, infusion, deposition, implantation, anal or vaginal suppision, oral ingestion, inhalation, topical administration, or any other method of administration where access to the target cells by the inhibitor is obtained. In some embodiments, topical administration is preferred, due to the high concentration of APCs in the skin. One method for accomplishing topical administration includes transdermal administration, such as iontophoresis. Iontophoretic transmission can be accomplished by using commercially-available patches that deliver a compound continuously through unbroken skin for periods of hours to days to weeks, depending on the particular patch. This method allows for the controlled delivery of the composition through the skin in relatively high concentrations. One example of an iontophoretic patch is the LECTRO PATCH™ sold by General Medical Company of Los Angeles, Calif. The patch provides dosages of different concentrations that can be continuously or periodically administered across the skin using electronic stimulation of reservoirs containing the composition. Topical administration also includes epidermal administration, which involves the mechanical or chemical irritation of the outermost layer of the epidermis sufficiently to provoke an immune response to the irritant. The irritant attracts APCs to the site of irritation where they can then take up the composition. One example of a mechanical irritant is a tyne-containing device. Such a device contains tynes that irritate the skin and deliver the drug at the same time, for instance, the MONO VACC™ manufactured by Pasteur Merieux of Lyon, France. The device contains a syringe plunger at one end and a tyne disk at the other. The tyne disk supports several narrow diameter tynes, which are capable of scratching the outermost layer of epidermal cells. Chemical irritants include, for instance, keratinolytic agents, such as salicylic acid, and can be used alone or in conjunction with other irritants such as mechanical irritants.

In certain embodiments of the invention, the administration of the composition of the invention may be designed so as to result in sequential exposures to the composition over a certain time period, for example, hours, days, weeks, months, or years. This may be accomplished, for example, by repeated administration of a composition of the invention by one of the methods described above, and/or by a sustained or controlled release delivery system in which the composition is delivered over a prolonged period, usually without repeated administrations. Administration of the composition using such a delivery system may be, for example, by oral dosage forms, bolus injections, transdermal patches or subcutaneous implants. Maintaining a substantially constant concentration of the composition may be desirable in some cases.

Other delivery systems suitable for use with the present invention include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides, hydrogel release systems, liposome-based systems, phospholipid based-systems, silastic systems, peptide based systems, wax coatings, compressed tablets using conventional binders and excipients, or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and 5,239,660), or diffusional systems in which an active component controls the release rate (for example, as described in U.S. Pat. Nos. 3,832,253, 3,854,480, 5,133,974 and 5,407,686). The formulation may be present as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention in some cases.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core-degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

In certain embodiments of the invention, a composition may include a suitable pharmaceutically acceptable carrier, for example, as incorporated into a liposome, incorporated into a polymer release system, or suspended in a liquid, e.g., in a dissolved form or a colloidal form, such as in a colloidal dispersion system. In general, pharmaceutically acceptable carriers suitable for use in the invention are well known to those of ordinary skill in the art. As used herein, a "pharmaceutically acceptable carrier" refers to a non-toxic material that does not significantly interfere with the effectiveness of the biological activity of the active compound(s) to be administered, but is used as a formulation ingredient, for example, to stabilize or protect the active compound(s) within the composition before use. The term "carrier" denotes an organic or inorganic ingredient, which may be natural or synthetic, with which one or more active compounds of the invention are combined to facilitate the application of the composition. The carrier may be co-mingled or otherwise mixed with one or more active compounds of the present invention, and with each other, in a manner such that there is no interaction that would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

As used herein, a "colloidal dispersion system" refers to a natural or synthetic molecule, other than those derived from bacteriological or viral sources, capable of delivering to and releasing the composition in a subject. Colloidal dispersion systems include macromolecular complexes, nanocapsules, microspheres, beads, and lipid-based systems including oil-in-water emulsions, micelles, mixed micelles, and liposomes. A preferred colloidal system of the invention is a liposome. Liposomes are artificial membrane vessels that are useful as a delivery vector in vivo or in vitro. It has been shown that large unilamellar vessels (LUV), which range in size from 0.2 micrometers to 4.0 micrometers can encapsulate large macromolecules within the aqueous interior and these macromolecules can be delivered to cells in a biologically active form (Fraley, et al., *Trends Biochem. Sci.*, 6:77, 1981).

Lipid formulations for transfection are commercially available, e.g., from QIAGEN, for example as EFFECTENE™ (a non-liposomal lipid with a special DNA condensing enhancer) and SUPER-FECT™ (a novel acting dendrimeric technology) as well as Gibco BRL, for example, as LIPOFECTIN™ and LIPOFECTACE™, which are formed of cationic lipids such as N-[1-(2,3-dioleyloxy)-propyl]-N,N,N-trimethylammonium chloride (DOTMA) and dimethyl dioctadecylammonium bromide (DDAB). Methods for making liposomes are well known in the art and have been described in many publications. Some liposomes were described in a review article by Gregoriadis, *Trends in Biotechnol.*, 3:235-241, 1985, which is hereby incorporated by reference.

In one embodiment, the vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System." PCT/US/0307 describes a biocompatible, preferably biodegradable polymeric matrix for containing an exogenous gene under the control of an appropriate promoter. The polymeric matrix is used to achieve sustained release of the exogenous gene in the subject. In accordance with the present invention, the compositions of the invention described herein can be encapsulated or dispersed within the biocompatible, optionally biodegradable polymeric matrix disclosed in PCT/US/03307.

The polymeric matrix can be in the form of a microparticle such as a microsphere (where the composition is dispersed throughout a solid polymeric matrix) or a microcapsule (where the composition is stored in the core of a polymeric shell). Other forms of the polymeric matrix for containing the composition include films, coatings, gels, implants, and stents. The size and composition of the polymeric matrix device can be selected to result in favorable release kinetics in the tissue into which the matrix is introduced. The size of the polymeric matrix can also be selected according to the method of delivery which is to be used, typically injection into a tissue or administration of a suspension by aerosol into the nasal and/or pulmonary areas. When an aerosol route is used the polymeric matrix and composition can be encompassed in a surfactant vehicle. The polymeric matrix composition can be selected to have both favorable degradation rates and/or to be formed of a material that is bioadhesive, e.g., to further increase the effectiveness of transfer when the matrix is administered to a nasal and/or pulmonary surface that has sustained an injury. The matrix composition can also be selected not to degrade, but rather, to release by diffusion over an extended period of time. In another embodiment, the matrix is a biocompatible microsphere that is suitable for oral delivery. Such microspheres are disclosed in Chickering, et al., *Biotech. and Bioeng.*, 52:96-101, 1996, and Mathiowitz, et al., *Nature*, 386:410-414, 1997.

Both non-biodegradable and biodegradable polymeric matrices can be used to deliver the compositions of the invention to the subject. Such polymers may be natural or synthetic polymers. The polymer may be selected based on the period of time over which release is desired, generally in the order of a few hours, to a year or longer. Typically, release over a period ranging from between a few hours and three to twelve months is desirable. The polymer optionally is in the form of a hydrogel that can absorb up to about 90% of its weight in water and further, optionally is cross-linked with multivalent ions or other polymers.

In some embodiments, the compositions of the invention may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc.

administrations can be found in, for example, *Remington's Pharmaceutical Sciences*, Mack Publishing Co. Those of ordinary skill in the art can readily determine the various parameters for preparing and formulating the compositions of the invention without resort to undue experimentation.

In some embodiments, the present invention includes the step of forming a composition of the invention by bringing an active compound into association or contact with a suitable carrier, which may constitute one or more accessory ingredients. The final composition may be prepared by any suitable technique, for example, by uniformly and intimately bringing the composition into association with a liquid carrier, a finely divided solid carrier or both, optionally with one or more formulation ingredients as previously described, and then, if necessary, shaping the product.

In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

In one aspect, the present invention provides any of the above-mentioned compositions in kits, optionally including instructions for use of the composition e.g., for the treatment of cancers or wounds. That is, the kit can include a description of use of the composition for participation in any biological or chemical mechanism disclosed herein associated with cancers or wounds. The kits can further include a description of activity of the cancers or wounds in treating the pathology, as opposed to the symptoms. The kit can include a description of use of the compositions as discussed herein. The kit also can include instructions for use of a combination of two or more compositions of the invention, or instruction for use of a combination of a composition of the invention and one or more other compounds indicated for treatment of a cancer, a wound, etc. Instructions also may be provided for administering the composition by any suitable technique as previously described, for example, orally, intravenously, pump or implantable delivery device, or via another known route of drug delivery.

The invention also involves, in another aspect, promotion of the treatment of cancers, wounds, etc. according to any of the systems or methods described herein. In some embodiments, one or more compositions of the invention may be promoted for treatment of cancers or wounds, or include instructions for treatment of cancers or wounds. In some cases, the invention provides a method involving promoting the prevention or treatment of cancers, wounds, etc. via administration of any one of the compositions of the present invention, and homologs, analogs, derivatives, enantiomers and functionally equivalent compositions thereof in which the invention is able to treat cancer, wounds, etc. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cancers or wounds. "Instructions" can define a component of promotion, and typically involve written instructions on or associated with packaging of compositions of the invention. Instructions also can include any oral or electronic instructions provided in any manner. The "kit" typically defines a package including one or more compositions of the invention and the instructions, or homologs, analogs, derivatives, enantiomers and functionally equivalent compositions thereof, but can also include a composition of the invention and instructions of any form that are provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions in some cases. The kits also can include other containers with one or more solvents, surfactants, preservative and/or diluents (e.g., normal saline (0.9% NaCl), or 5% dextrose) as well as containers for mixing, diluting or administering the components to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the active compound(s) within the composition and the mode of use or administration. Suitable solvents are well known, for example as previously described, and are available in the literature. The solvent will depend on the compound and the mode of use or administration.

While several embodiments of the invention have been described and illustrated herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention.

All definitions as used herein are solely for the purposes of this disclosure. These definitions should not necessarily be imputed to other commonly-owned patents and/or patent applications, whether related or unrelated to this disclosure. The definitions, as used herein, should be understood to control over dictionary definitions, definitions in documents incorporated by reference, and/or ordinary meanings of the defined terms.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising:
administering to a subject having cancer a therapeutically acceptable amount of (a) an isolated glycolytic inhibitor, wherein the isolated glycolytic inhibitor is 2-deoxy-D-glucose or a pharmaceutically acceptable salt thereof (b) an isolated fatty acid metabolism inhibitor, wherein the isolated fatty acid inhibitor is etomoxir or a pharmaceutically acceptable salt thereof, and (c) an anti-Fas antibody in a therapeutically acceptable amount to treat the cancer.

2. The method of claim 1, further comprising administering to the subject an anti-cancer agent.

3. The method of claim 1, wherein the cancer is drug-resistant.

4. The method of claim 1, wherein the cancer is multi-drug resistant.

5. The method of claim 1, wherein the therapeutically acceptable amount is in an amount cytotoxic to the cancer cells.

6. The method of claim 1, wherein the subject is not indicated for treatment for obesity.

7. The method of claim 1, wherein a majority of cells comprising the cancer derive a majority of their metabolic energy through fatty acid metabolism.

8. The method of claim 1 further comprising surgically removing a tumor from a subject and inserting, into a site within the subject where the tumor was removed therefrom: (a) said glycolytic inhibitor (b) said fatty acid metabolism inhibitor and said anti-Fas antibody.

9. The method of claim 1, further comprising administering to the subject an anti-UCP antibody.

10. The method of claim 1, further comprising administering to the subject radiotherapy.

* * * * *

SEQUENCE LISTING

```
<160> NUMBER OF SEQ ID NOS: 6

<210> SEQ ID NO 1
<211> LENGTH: 924
<212> TYPE: DNA
<213> ORGANISM: Homo sapiens

<400> SEQUENCE: 1 atgggggggcc tgacagcctc ggacgtacac ccgaccctgg gggtccagct cttctcagct      60
ggaatagcgg cgtgcttggc ggacgtgatc accttcccgc tggacacggc caaagtccgg     120
ctccaggtcc aaggtgaatg cccgacgtcc agtgttatta ggtataaagg tgtcctggga     180
acaatcaccg ctgtggtaaa aacagaaggg cggatgaaac tctacagcgg gctgcctgcg     240
gggcttcagc ggcaaatcag ctccgcctct ctcaggatcg gcctctacga cacggtccag     300
gagttcctca ccgcagggaa agaaacagca cctagtttag gaagcaagat tttagctggt     360
ctaacgactg gaggagtggc agtattcatt gggcaaccca cagaggtcgt gaaagtcaga     420
cttcaagcac agagccatct ccacggaatc aaacctcgct acacggggac ttataatgcg     480
tacagaataa tagcaacaac cgaaggcttg acgggtcttt ggaaagggac tactcccaat     540
ctgatgagaa gtgtcatcat caattgtaca gagctagtaa catatgatct aatgaaggag     600
gcctttgtga aaaacaacat attagcagat gacgtcccct gccacttggt gtcggctctt     660
atcgctggat tttgcgcaac agctatgtcc tccccggtgg atgtagtaaa aaccagattt     720
attaattctc caccaggaca gtacaaaagt gtgcccaact gtgcaatgaa agtgttcact     780
aacgaaggac caacggcttt cttcaagggg ttggtaccct ccttcttgcg acttggatcc     840
tggaacgtca ttatgtttgt gtgctttgaa caactgaaac gagaactgtc aaagtcaagg     900
cagactatgg actgtgccac ataa                                            924

<210> SEQ ID NO 2
<211> LENGTH: 307
<212> TYPE: PRT
<213> ORGANISM: Homo sapiens

<400> SEQUENCE: 2

Met Gly Gly Leu Thr Ala Ser Asp Val His Pro Thr Leu Gly Val Gln
1               5                   10                  15

Leu Phe Ser Ala Gly Ile Ala Ala Cys Leu Ala Asp Val Ile Thr Phe
            20                  25                  30

Pro Leu Asp Thr Ala Lys Val Arg Leu Gln Val Gln Gly Glu Cys Pro
```

-continued

```
            35                  40                  45
Thr Ser Ser Val Ile Arg Tyr Lys Gly Val Leu Gly Thr Ile Thr Ala
 50                  55                  60
Val Val Lys Thr Glu Gly Arg Met Lys Leu Tyr Ser Gly Leu Pro Ala
 65                  70                  75                  80
Gly Leu Gln Arg Gln Ile Ser Ser Ala Ser Leu Arg Ile Gly Leu Tyr
                 85                  90                  95
Asp Thr Val Gln Glu Phe Leu Thr Ala Gly Lys Glu Thr Ala Pro Ser
            100                 105                 110
Leu Gly Ser Lys Ile Leu Ala Gly Leu Thr Thr Gly Val Ala Val
            115                 120                 125
Phe Ile Gly Gln Pro Thr Glu Val Val Lys Val Arg Leu Gln Ala Gln
        130                 135                 140
Ser His Leu His Gly Ile Lys Pro Arg Tyr Thr Gly Thr Tyr Asn Ala
145                 150                 155                 160
Tyr Arg Ile Ile Ala Thr Thr Glu Gly Leu Thr Gly Leu Trp Lys Gly
                165                 170                 175
Thr Thr Pro Asn Leu Met Arg Ser Val Ile Ile Asn Cys Thr Glu Leu
            180                 185                 190
Val Thr Tyr Asp Leu Met Lys Glu Ala Phe Val Lys Asn Asn Ile Leu
        195                 200                 205
Ala Asp Asp Val Pro Cys His Leu Val Ser Ala Leu Ile Ala Gly Phe
    210                 215                 220
Cys Ala Thr Ala Met Ser Ser Pro Val Asp Val Val Lys Thr Arg Phe
225                 230                 235                 240
Ile Asn Ser Pro Pro Gly Gln Tyr Lys Ser Val Pro Asn Cys Ala Met
                245                 250                 255
Lys Val Phe Thr Asn Glu Gly Pro Thr Ala Phe Phe Lys Gly Leu Val
            260                 265                 270
Pro Ser Phe Leu Arg Leu Gly Ser Trp Asn Val Ile Met Phe Val Cys
        275                 280                 285
Phe Glu Gln Leu Lys Arg Glu Leu Ser Lys Ser Arg Gln Thr Met Asp
    290                 295                 300
Cys Ala Thr
305

<210> SEQ ID NO 3
<211> LENGTH: 1105
<212> TYPE: DNA
<213> ORGANISM: Homo sapiens

<400> SEQUENCE: 3
gttcctctat ctcgtcttgt tgctgattaa aggtgcccct gtctccagtt tttctccatc     60
tcctgggacg tagcaggaaa tcagcatcat ggttgggttc aaggccacag atgtgccccc    120
tactgccact gtgaagtttc ttggggctgg cacagctgcc tgcatcgcag atctcatcac    180
ctttcctctg gatactgcta aagtccggtt acagatccaa ggagaaagtc aggggccagt    240
gcgcgctaca gccagcgccc agtaccgcgg tgtgatgggc accattctga ccatggtgcg    300
tactgagggc ccccgaagcc tctacaatgg gctggttgcc ggcctgcagc gccaaatgag    360
ctttgcctct gtccgcatcg gcctgtatga ttctgtcaaa cagttctaca ccaagggctc    420
tgagcatgcc agcattggga gccgcctcct agcaggcagc accacaggtg ccctggctgt    480
ggctgtggcc cagcccacgg atgtggtaaa ggtccgattc aagctcagg cccgggctgg    540
```

-continued

```
aggtggtcgg agataccaaa gcaccgtcaa tgcctacaag accattgccc gagaggaagg      600
gttccggggc ctctggaaag ggacctctcc caatgttgct cgtaatgcca ttgtcaactg      660
tgctgagctg gtgacctatg acctcatcaa ggatgccctc ctgaaagcca acctcatgac      720
agatgacctc ccttgccact tcacttctgc ctttggggca ggcttctgca ccactgtcat      780
cgcctcccct gtagacgtgg tcaagacgag atacatgaac tctgccctgg gccagtacag      840
tagcgctggc cactgtgccc ttaccatgct ccagaaggag gggccccgag ccttctacaa      900
agggttcatg ccctcctttc tccgcttggg ttcctggaac gtggtgatgt tcgtcaccta      960
tgagcagctg aaacgagccc tcatggctgc ctgcacttcc cgagaggctc ccttctgagc    1020
ctctcctgct gctgacctga tcacctctgg ctttgtctct agccgggcca tgctttcctt    1080
ttcttccttc tttctcttcc ctccg                                          1105
```

<210> SEQ ID NO 4
<211> LENGTH: 309
<212> TYPE: PRT
<213> ORGANISM: Homo sapiens

<400> SEQUENCE: 4

```
Met Val Gly Phe Lys Ala Thr Asp Val Pro Thr Ala Thr Val Lys
1               5                   10                  15

Phe Leu Gly Ala Gly Thr Ala Ala Cys Ile Ala Asp Leu Ile Thr Phe
            20                  25                  30

Pro Leu Asp Thr Ala Lys Val Arg Leu Gln Ile Gln Gly Glu Ser Gln
        35                  40                  45

Gly Pro Val Arg Ala Thr Ala Ser Ala Gln Tyr Arg Gly Val Met Gly
    50                  55                  60

Thr Ile Leu Thr Met Val Arg Thr Glu Gly Pro Arg Ser Leu Tyr Asn
65                  70                  75                  80

Gly Leu Val Ala Gly Leu Gln Arg Gln Met Ser Phe Ala Ser Val Arg
                85                  90                  95

Ile Gly Leu Tyr Asp Ser Val Lys Gln Phe Tyr Thr Lys Gly Ser Glu
            100                 105                 110

His Ala Ser Ile Gly Ser Arg Leu Leu Ala Gly Ser Thr Thr Gly Ala
        115                 120                 125

Leu Ala Val Ala Val Ala Gln Pro Thr Asp Val Lys Val Arg Phe
    130                 135                 140

Gln Ala Gln Ala Arg Ala Gly Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
            180                 185                 190

Glu Leu Val Thr Tyr Asp Leu Ile Lys Asp Ala Leu Leu Lys Ala Asn
        195                 200                 205

Leu Met Thr Asp Asp Leu Pro Cys His Phe Thr Ser Ala Phe Gly Ala
    210                 215                 220

Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
            260                 265                 270
```

```
Phe Met Pro Ser Phe Leu Arg Leu Gly Ser Trp Asn Val Val Met Phe
        275                 280                 285

Val Thr Tyr Glu Gln Leu Lys Arg Ala Leu Met Ala Ala Cys Thr Ser
        290                 295                 300

Arg Glu Ala Pro Phe
305

<210> SEQ ID NO 5
<211> LENGTH: 1132
<212> TYPE: DNA
<213> ORGANISM: Homo sapiens

<400> SEQUENCE: 5
tcctgggatg gagccctagg gagcccctgt gctgccctg ccgtggcagg actcacagcc     60
ccaccgctgc actgaagccc agggctgtgg agcagcctct ctccttggac ctcctctcgg    120
ccctaaaggg actgggcaga gccttccagg actatggttg gactgaagcc ttcagacgtg    180
cctcccacca tggctgtgaa gttcctgggg gcaggcacag cagcctgttt tgctgacctc    240
gttacctttc cactggacac agccaaggtc cgcctgcaga tccagggga gaaccaggcg    300 gtccagacgg cccggctcgt gcagtaccgt ggcgtgctgg gcaccatcct gaccatggtg    360
cggactgagg gtccctgcag ccctacaat gggctggtgg ccggcctgca gcgccagatg    420
agcttcgcct ccatccgcat cggcctctat gactccgtca gcaggtgta cacccccaaa     480 ggcgcggaca ctccagcct cactacccgg attttggccg gctgcaccac aggagccatg    540
gcggtgacct gtgcccagcc cacagatgtg gtgaaggtcc gatttcaggc cagcatacac    600
ctcgggccat ccaggagcga cagaaaatac agcgggacta tggacgccta cagaaccatc    660
gccagggagg aaggagtcag gggcctgtgg aaaggaactt tgcccaacat catgaggaat    720
gctatcgtca actgtgctga ggtggtgacc tacgacatcc tcaaggagaa gctgctggac    780
taccacctgc tcactgacaa cttccctgc cactttgtct ctgcctttgg agccggcttc    840
tgtgccacag tggtggcctc cccggtggac gtggtgaaga cccggtatat gaactcacct    900
ccaggccagt acttcagccc cctcgactgt atgataaaga tggtggccca ggagggcccc    960
acagccttct acaaggggtg agcctcctcc tgcctccagc actccctccc agagaacagg   1020 ggcttcttc ttttcgaatg tggctaccgt gggtcaacct gggatgtagc ggtgaagagt   1080
acagatgtaa atgccacaaa gaagaagttt aaaaaaccat gcaaaaaaaa aa           1132

<210> SEQ ID NO 6
<211> LENGTH: 275
<212> TYPE: PRT
<213> ORGANISM: Homo sapiens

<400> SEQUENCE: 6

Met Val Gly Leu Lys Pro Ser Asp Val Pro Thr Met Ala Val Lys
1               5                   10                  15

Phe Leu Gly Ala Gly Thr Ala Ala Cys Phe Ala Asp Leu Val Thr Phe
                20                  25                  30

Pro Leu Asp Thr Ala Lys Val Arg Leu Gln Ile Gln Gly Glu Asn Gln
        35                  40                  45

Ala Val Gln Thr Ala Arg Leu Val Gln Tyr Arg Gly Val Leu Gly Thr
    50                  55                  60

Ile Leu Thr Met Val Arg Thr Glu Gly Pro Cys Ser Pro Tyr Asn Gly
65                  70                  75                  80

Leu Val Ala Gly Leu Gln Arg Gln Met Ser Phe Ala Ser Ile Arg Ile
```

-continued

```
                    85                  90                  95
Gly Leu Tyr Asp Ser Val Lys Gln Val Tyr Thr Pro Lys Gly Ala Asp
            100                 105                 110

Asn Ser Ser Leu Thr Thr Arg Ile Leu Ala Gly Cys Thr Thr Gly Ala
            115                 120                 125

Met Ala Val Thr Cys Ala Gln Pro Thr Asp Val Val Lys Val Arg Phe
            130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
            180                 185                 190

Asn Cys Ala Glu Val Val Thr Tyr Asp Ile Leu Lys Glu Lys Leu Leu
            195                 200                 205

Asp Tyr His Leu Leu Thr Asp Asn Phe Pro Cys His Phe Val Ser Ala
        210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
            260                 265                 270

Tyr Lys Gly
        275
```